US007153864B2

United States Patent
Bhatt et al.

(10) Patent No.: US 7,153,864 B2
(45) Date of Patent: Dec. 26, 2006

(54) POLYGLUTAMIC ACID-CAMPTOTHECIN CONJUGATES AND METHODS OF PREPARATION

(75) Inventors: Rama Bhatt, Shoreline, WA (US); Peter de Vries, Seattle, WA (US); J. Peter Klein, Vashon, WA (US); John Tulinsky, Seattle, WA (US); Robert A. Lewis, Mendham, NJ (US); Jack W. Singer, Seattle, WA (US)

(73) Assignee: Cell Therapeutics Inc., Seattle, WA (US)

( * ) Notice: Subject to any disclaimer, the term of this patent is extended or adjusted under 35 U.S.C. 154(b) by 406 days.

(21) Appl. No.: 10/407,218

(22) Filed: Apr. 7, 2003

(65) Prior Publication Data

US 2003/0211973 A1 Nov. 13, 2003

Related U.S. Application Data

(63) Continuation of application No. 09/956,237, filed on Mar. 19, 2001, now abandoned, which is a continuation-in-part of application No. 09/810,345, filed on Mar. 19, 2001, now abandoned.

(60) Provisional application No. 60/190,429, filed on Mar. 17, 2000.

(51) Int. Cl.
*A01N 43/42* (2006.01)
*A61K 31/44* (2006.01)
*A01N 43/40* (2006.01)

(52) U.S. Cl. .................. 514/280; 514/183; 514/277; 514/279; 514/332; 424/78.08

(58) Field of Classification Search ............... 514/183, 514/277, 279, 280, 332, 449, 451, 476; 424/78.08
See application file for complete search history.

(56) References Cited

U.S. PATENT DOCUMENTS

| 4,356,166 | A | 10/1982 | Peterson et al. |
|---|---|---|---|
| 4,942,184 | A | 7/1990 | Haugwitz et al. |
| 4,943,579 | A | 7/1990 | Vishnuvajjala et al. |
| 4,960,790 | A | 10/1990 | Stella et al. |
| 5,059,699 | A | 10/1991 | Kingston et al. |
| 5,087,616 | A | 2/1992 | Myers et al. |
| 5,169,933 | A | 12/1992 | Anderson et al. |
| 5,219,564 | A | 6/1993 | Zalipsky et al. |
| 5,340,817 | A | 8/1994 | Wall et al. |
| 5,362,831 | A | 11/1994 | Mongelli |
| 5,380,751 | A | 1/1995 | Chen et al. |
| 5,422,364 | A | 6/1995 | Nicolaou et al. |
| 5,468,769 | A | 11/1995 | Klein et al. |
| 5,473,055 | A | 12/1995 | Mongelli et al. |
| 5,489,525 | A | 2/1996 | Pastan |
| 5,545,880 | A | 8/1996 | Bu et al. |
| 5,569,720 | A | 10/1996 | Mongelli et al. |
| 5,583,153 | A | 12/1996 | Brahn |
| 5,607,659 | A | 3/1997 | Gustavson et al. |
| 5,614,549 | A | 3/1997 | Greenwald et al. |
| 5,621,001 | A | 4/1997 | Canetta et al. |
| 5,626,862 | A | 5/1997 | Brem et al. |
| 5,629,433 | A | 5/1997 | Zheng et al. |
| 5,641,803 | A | 6/1997 | Carretta et al. |
| 5,646,159 | A | 7/1997 | Wall et al. |
| 5,648,506 | A | 7/1997 | Desai et al. |
| 5,716,981 | A | 2/1998 | Hunter et al. |
| 5,719,265 | A | 2/1998 | Mongelli et al. |
| 5,730,968 | A | 3/1998 | Butterfield et al. |
| 5,733,925 | A | 3/1998 | Kunz et al. |
| 5,762,909 | A | 6/1998 | Uzgiris |
| 5,773,522 | A | 6/1998 | Angelucci et al. |
| 5,776,925 | A | 7/1998 | Young et al. |
| 5,783,178 | A | 7/1998 | Kabanov et al. |
| 5,811,447 | A | 9/1998 | Kunz et al. |
| 5,837,673 | A | 11/1998 | Tsujihara et al. |
| 5,846,565 | A | 12/1998 | Brem et al. |
| 5,854,006 | A | 12/1998 | Hanigan et al. |
| 5,873,904 | A | 2/1999 | Ragheb et al. |
| 5,880,131 | A | 3/1999 | Greenwald et al. |
| 5,886,026 | A | 3/1999 | Hunter et al. |
| 5,892,043 | A | 4/1999 | Tsujihara et al. |
| 5,916,896 | A | 6/1999 | Wall et al. |
| 5,977,163 | A | 11/1999 | Li et al. |
| 5,981,568 | A | 11/1999 | Kunz et al. |
| 6,005,020 | A | 12/1999 | Loomis |
| 6,011,042 | A | 1/2000 | Greenwald et al. |
| 6,028,164 | A | 2/2000 | Loomis |
| 6,127,355 | A | 10/2000 | Greenwald et al. |
| 6,218,367 | B1 | 4/2001 | Jacob |
| 6,262,107 | B1 * | 7/2001 | Li et al. ............. 514/449 |
| 2001/0034363 | A1 | 10/2001 | Li et al. |
| 2001/0041189 | A1 | 11/2001 | Xu |
| 2002/0016285 | A1 | 2/2002 | Bhatt et al. |

FOREIGN PATENT DOCUMENTS

| EP | 0589281 B1 | 3/1996 |
|---|---|---|
| EP | 0558959 B1 | 4/1997 |
| EP | 0604910 B1 | 6/2000 |
| JP | 5286868 A | 11/1993 |

(Continued)

OTHER PUBLICATIONS

Caiolfa et al. Journal of Controlled Release (2000), vol. 65, pp. 105-119.*

(Continued)

*Primary Examiner*—Patrick Lewis
(74) *Attorney, Agent, or Firm*—Foley & Lardner LLP

(57) ABSTRACT

The invention provides polyglutamic acid-therapeutic agent conjugates and methods for their preparation and use.

67 Claims, 1 Drawing Sheet

FOREIGN PATENT DOCUMENTS

| WO | WO 93/10121 A1 | 5/1993 |
| --- | --- | --- |
| WO | WO 95/03036 A1 | 2/1995 |
| WO | WO 95/13053 A1 | 5/1995 |
| WO | WO 96/25176 A1 | 8/1996 |
| WO | WO 97/33552 A1 | 9/1997 |
| WO | WO 99/17804 A1 | 4/1999 |
| WO | WO 99/49901 A1 | 10/1999 |
| WO | WO 01/70275 A2 | 9/2001 |

OTHER PUBLICATIONS

Greenwald et al Bioorganic & Medicinal Chemistry (1998), vol. 6, pp. 551-562.*

Balog et al., "Total Synthesis of (–) Epothilone A," *Angew. Chem. Int. Ed. Engl.*, vol. 35, 1996, pp. 2801-2803 © VCH Verlagsgesellschaft mbH, Weinheim.

Bartoli et al., "*In Vitro* and *In Vivo* Antitumoral Activity of Free, and Encapsulated Taxol," *J. Microencapsulation*, vol. 7, 1990, pp. 191-197 © Taylor & Francis Ltd.

Bom et al., "The Novel Silatecan 7-*tert*-Butyldimethylsilyl-10-hydroxycamptothecin Displays High Lipophilicity, Improved Human Blood Stability, and Potent Anticancer Activity," *Journal of Medicinal Chemistry*, vol. 43, No. 21, 2000, pp. 3970-3980, © American Chemical Society.

Borman, "Epothilone Epiphany: Total Syntheses," *C&EN*, vol. 74, 1996, pp. 24-26 © American Chemical Society.

Caiolfa et al., "Polymer-bound camptothecin: initial biodistribution and antitumor activity studies," *Journal of Controlled Release*, Rel. 65, pp. 105-119, © Elsevier Science B.V., Amsterdam, 2000.

Conover et al, "Camptothecin delivery systems: the utility of amino acid spacers for the conjugation of camptothecin with polyethylene glycol to create prodrugs," *Anti-Cancer Drug Design*, vol. 14, pp. 499-506, © Oxford University Press, 1999.

Conover et al., "Camptothecin delivery systems: enhanced efficacy and tumor accumulation of camptothecin following its conjugation to polyethylene glycol via a glycine linker," *Cancer Chemother Pharmacol*, vol. 42, 1998, pp. 407-414, © Springer-Verlag.

Conover et al., "Camptothecin Delivery Systems: The Antitumor Activity of a Camptothecin-20-0-Polyethylene Glycol Ester Transport Form," *Anticancer Research*, vol. 17, 1997, pp. 3361-3368.

Conover et al., "Camptothecin Delivery Systems: The Utility of Amino Acid Spacers for the Conjugation of Camptothecin with Polyethylene Glycol to Create Prodrugs," *Anti-Cancer Drug Design*, vol. 14, 1999, pp. 499-506, © Oxford University Press.

Conover et al., Camptothecin Delivery Systems: The Antitumor Activity of a Camptothecin-20-0-Polyethylene Glycol Ester Transport Form, *Anticancer Research*, vol. 17, pp. 3361-3368, 1997.

Cortes et al., "Docetaxel," *J. of Clinical Oncolgy*, vol. 13, 1995, pp. 2643-2655 © American Society of Clinical Oncology.

de Bono et al., "Phase I Pharmacokinetic (PK) Study of Mag-CPT-(PNO 166148) A Polymer Derivative of Camptothecin (CPT)," *Pharmicia*.

De Vries et al., "Conjugation of Docetaxel (DTXL) to Poly L-Glutamic Acid (PG) Increases Anti-Tumor Efficacy," *Proceedings of the American Association for Cancer Research*, vol. 41, 2000, p. 323, Abstract No. 2051.

De Vries et al., "CT-2103: A water soluble poly-L-glutamic acid (PG)-Paclitaxesl (TXL) conjugate has enhanced efficacy on MDR-1+human colon carcinoma cell line xenografts compared to free TXL," *AACR*, 2001, Abstract No. 462.

De Vries et al., "Optimization of the anti-tumor activity of water-soluble poly L-glutamic acid (PG)-paclitaxel (TXL) conjugates," *AACR-NCI-EORTC 92*, 1999, p. 22, Abstract No. 451, Washington, DC.

De Vries et al., "Pharmacokinetics (PK) and biodistribution of poly-(L)-glutamic acid (PG) paclitaxesl (TXL) (CT-2103) in mice with subcutaneous B-16 melanomas," *Proceedings of the 11th AACR-NCI-EORTC Symposium*, 2000 Amsterdam, Netherlands.

Deutsch et al., "Synthesis of Congeners of Prodrugs. 3. Water-Soluble Prodrugs of Taxol with Potent Antitumor Activity," *J. Med. Chem.*, vol. 32, 1989, pp. 788-792 © American Chemical Society.

Duncan et al., "Polymer-drug conjugates, PDEPT and PELT: basic principles for design and transfer from the Laboratory to Clinic," *Journal of Controlled Release*, vol. 74, 2001, pp. 135-146, © Elsevier Science B.V.

Eiseman et al , "Plasma pharmcokinetics and tissue distribution of paclitaxel in CD2F1 mice," *Cancer Chemother. Pharmacol.*, vol. 34, 1994, pp. 465-471 © Springer-Verlag.

Fidler et al., "The Biology of Cancer Invasion and Metastasis," *Adv. Cancer Res.*, vol. 28, 1978, pp. 149-250 © Academic Press, Inc.

Gilbert et al.. "Novel water soluble paclitaxel derivatives: Evaluation of PEG-paclitaxel's *in vitro* and *in vivo* effects," *Proc. Amer. Assoc. Cancer Res.*, vol. 38, 1997, p. 225, Abstract #1512.

Goldspiel, "Pharmaceutical Issues: Preparation, Administration, Stability, and Compatibility with Other Medications," *Ann. Pharmacotherapy*, vol. 28, 1994, pp. S23-S26, © Harvey Whitney Books Company.

Greenwald et al , "Camptothecin-20-PEG Ester Transport Forms: the Effect of Spacer Groups on Antitumor Activity," *Bioorganic & Medicinal Chemistry*, vol. 6, pp. 551-562, © Elsevier Science Ltd., Amsterdam, 1998.

Greenwald et al , "Drug Delivery Systems. 2. Camptothecin 20-*0*-Poly(ethylene glycol) Ester Transport Forms," *J. Med Chem.*, vol. 39, 1996, pp. 1938-1940, © American Chemical Society.

Greenwald et al , "Drug Delivery Systems: Water Soluble Taxol 2'-Poly(Ethylene Glycol) Ester Prodrugs-Design and *in Vivo* Effectiveness," *J. Med Chem.*, vol. 39, 1996, pp. 424-431 © American Chemical Society.

Greenwald et al , "Highly Water Soluble Taxol Derivatives: 2'-Polyethylene Glycol Esters as Potential Products," *J. Org. Chem.*, vol. 60, 1995, pp. 331-336 © American Chemical Society.

Greenwald et al , "Highly Water Soluble Taxol Derivatives: 2'-polyethyleneglycol esters as potential prodrugs," *Bioorganic & Medicinal Chemistry Letters*, vol. 4, 1994, pp. 2465-2470 © Elsevier Science Ltd.

Greenwald et al , "Stereoselective acylation of 20-(S)-camptothecin with amino acid derivatives using scandium triflate/DMAP," *Tetrahedron: Asymmetry*, vol. 9, pp. 915-918, © Elsevier Science Ltd., Amsterdam, 1998.

Greenwald, "Camptothecin-20-PEG Ester Transport Forms: the Effect of Spacer Groups on Antitumor Activity", *Bioorganic & Medicinal Chemistry*, vol. 6, 1998, pp. 551-562 © Elsevier Science Ltd.

Hirano et al., "Polymeric derivatives of activated cyclophosphamide as drug delivery systems in antitumor therapy pharmacologically active polymers, 20," *Makromol. Chem.*, vol. 180, 1979, pp. 1125-1130 © Huthig & Wepf Verlag, Basel, Heidelberg.

Hoes et al., "Optimization of macromolecular prodrugs of the antitumor antibiotic adriamycin," *J. Controlled Release*, vol. 2, 1985, pp. 205-213 © Elsevier Science Publishers B.V.

Höfle et al., "Epothilone A and B—novel 16-membered macrolides with cytotoxic activity: isolation, crystal structure, and conformation in solution," *Angew. Chem. Int. Ed. Engl.*, vol. 35, 1996, pp. 1567-1569 © VCH Verlagsgesellschaft mbH.

Horwitz et al., "Taxol, mechanisms of action and resistance," *J. Natl. Cancer Inst. Monographs*, vol. 15, 1993, pp. 55-61.

Kato et al., "Antitumor activity of 1-β-$_D$-arabinofuranosylcytosine conjugated with polyglutamic acid and its derivative," *Cancer Res.*, vol. 44, 1984, pp. 25-30.

Ke et al., "Elevated serum VEGF as a prognosis marker in combined radiation and PG-TXL (CT-2103) therapy in mice with murine ovarian OCa-1 tumor," *Proc Amer Assoc Cancer Res*, vol. 42, 2001, Abstract No. 3873.

Ke et al., "Potentiation of radioresponse by polymer-drug conjugates," *J.Control Release*, vol. 74, 2001, pp. 237-242 © Elsevier Science B.V.

Ke et al., "Schedule-independent radiosensitization of a murine ovarian OCa-1 tumor by PG-TXL," *Proc Am Assoc Cancer Res*, vol. 40, 1999, Abstract No. 4223.

Kopecek, "The potential of water-soluble polymeric carriers in targeted and site-specific drug delivery," *J. Controlled Release*, vol. 11, 1990, pp. 279-290 © Elsevier Science Publishers B.V.

Kouskoff et al., "Organ-specific disease provoked by systemic autoimmunity," *Cell*, vol. 87, 1996, pp. 811-822 © Cell Press.

Kuang et al., "Poly(benzyl-l-glutamate) microcapsules: Their diagnostic and therapeutic potential," *Pharm Res.*, vol. 10. 1993, p. S-191, Abstract PDD 7066 © Plenum Press.

Li et al, "Antitumor activity of Poly(L-glutamic acid)-Paclitaxel on syngeneic and xenografted tumors," *Proc Am Assoc Cancer Res*, vol. 40, 1999, Abstract No. 1909.

Li et al, "Antitumor activity of Poly(L-glutamic acid)-Paclitaxel on syngeneic and xenografted tumors," *Clin Cancer Res*, vol. 5, 1999, pp. 891-897.

Li et al, "Biodistribution of paclitaxel and poly(L-glutamic acid)-paclitaxel conjugate in mice with ovarian OCa-1 tumor," *Cancer Chemother Pharmacol*, vol. 46, 2000, pp. 416-422 © Springer-Verlag.

Li et al, "Complete regression of well-established tumors using a novel water-soluble poly(L-glutamic acid)-paclitaxel conjugate," *Cancer Res*, vol. 58, 1998, pp. 2404-2409.

Li et al, "Cytotoxic and antitumor activity of water-soluble paclitaxel prodrug," *Proc. Amer. Assoc. Cancer Res*, vol. 37, 1996, pp. 376-377, Abstract No. 2570.

Li et al, "Enhancement of tumor radioresponse of a murine ovarian carcinoma by poly(L-glutamic acid)-paclitaxel conjugate," *Ninth International Symposium on Recent Advances in Drug Delivery Systems*, 1999, Salt Lake City, UT.

Li et al, "Formation and characterization of CDDP loaded poly(benzyl L-glutamate) and poly (dl-lactic acid) microcarpsules for chemoemboization," *Proc. Amer. Assoc. Cancer Res.*, vol. 35, 1994, p. 336, Abstract No. 2003.

Li et al, "Potentiation of ovarian OCa-1 tumor radioresponse by poly (L-glutamic acid)-paclitaxel conjugate," *Int.J Radiat. Oncol. Biol. Phys.*, vol. 48, 2000, pp. 1119-1126 © Elsevier Science Inc.

Li et al, "Synthesis and evaluation of PEG-paclitaxel conjugate as a water-soluble paclitaxel prodrug," *Proc. Amer. Assoc. Cancer Res*, vol. 37, 1996, p. 376, Abstract No. 2569.

Li et al, "Synthesis and evaluation of water-soluble polyethylene glycol-paclitaxel conjugates as a paclitaxel prodrug," *Anticancer Drugs*, vol. 7, 1996, pp. 642-618.

Li et al, "Synthesis. biodistribution and imaging properties of indium-111-DTPA-paclitaxel in mice bearing mammary tumors," *J. Nucl. Med.*, vol. 38, 1997, pp. 1042-1047.

Li et al, "Tumor irradiation enhances the tumor-specific distribution of poly(L-glutamic acid)-conjugated paclitaxel and its antitumor efficacy," *Clin Cancer Res*, vol. 6, 2000, pp. 2829-2834.

Li et al, "Water-soluble polyglutamic acid paclitaxel conjugate (PGA-paclitaxel): antitumor regression in rats braeing 13762 mammary carcinoma," *American Association Pharmaceutical Scientists Meeting*, vol. 13, 1996, p. S368.

Maeda et al., "Tumoritropic and lymphotropic principles of macromolecular drugs," *Critical Reviews in Therapeutic Drug Carrier Systems*, vol. 6, 1989, pp. 193-210 © CRC Press.

Magri et al., "Modified Taxols. 2. Oxidation Products of Taxol," *J. Org Chem.*, vol. 51, 1986, pp. 797-802 © American Chemical Society.

Mason et al., "Poly (L-glutamic Acid)-paclitaxel dramatically enhances the anti-tumor efficacy of radiotherapy," *AACR—NCI—EORTC*, vol. 397, 2001, Miami Beach, Florida.

Mathew et al., "Synthesis and evaluation of some water-soluble prodrugs and derivatives of taxol with antitumor activity," *J. Med. Chem.*, vol. 35, 1992, pp. 145-151 © American Chemical Society.

Morimoto et al., "Antitumor agent poly (amino acid) conjugates as a drug carrier in cancer chemotherapy," *J. Pharm. Dyn.*, vol. 7, 1984, pp. 688-698.

Mosmann, "Rapid colorimetric assay for cellular growth and survival: application to proliferation and cytotoxic assay," *J. Immunol. Methods*, vol. 65, 1983, pp. 55-63 © Elsevier Science Publishers B.V.

Multani et al., "Paclitaxel and water-soluble poly (L-gluatmic acid)-paclitaxel, induce direct chromosomal Abnormalities and cell death in a murine metastatic melanoma cell line," *Anticancer Res*, vol. 17. 1997, pp. 4269-4274.

Oliver et al., "Suppression of collagen-induced arthritis using an angiogenesis inhibitor, AGM-1470, and a microtubule stabilizer, Taxol," *Cellular Immunology*, vol. 157, 1994, pp. 291-299 © Academic Press, Inc.

Pesenti et al., "Synthesis and biological activity of water soluble polymer-bound taxol derivatives," *Proc. Amer. Assoc Cancer Res.*, vol. 36, 1995, p. 307, Abstract No. 1824.

Phillips-Hughes et al, "Restenosis: pathophysiology and preventive strategies," *JVIR*, vol. 7, 1996, pp. 321-333 © SCVIR.

Pratesi et al., "Poly-L-Aspartic Acid as a Carrier for Doxorubicin: A Comparative *in vivo* Study of Free and Polymer-Bound Drug," *Br. J. Cancer*, vol. 52, 1985, pp. 841-848 © The Macmillan Press Ltd.

Reynolds et al., "Polymers help guide cancer drugs to tumor targets-and keep them there,"*J. Natl. Cancer Institute*, vol. 87, 1995, pp. 1582-1584.

Rose et al., "Preclinical antitumor activity of water-soluble paclitaxel derivatives," *Cancer Chemother. Pharmacol.*, vol. 39, 1997, pp. 486-492 © Springer Verlag.

Scudiero et al., "Evaluation of a soluble tetrazolium/formazan assay for cell growth and drug sensitivity in culture using human and other tumor cell lines," *Cancer Research*, vol. 48, 1988, pp. 4827-4833.

Serruys et al., "A comparison of balloon-expandable-stent implantation with balloon angioplasty in patients with coronary artery disease," *N. Engl. J. Med.*, vol. 331, 1994, pp. 489-495 © The Massachusetts Medical Society.

Shaffer et al., "*In vivo* identification of monoglutamyl paclitaxel metabolite from poly-L-glutamic acid-paclitaxel (CT-2103) in tumor bearing mice," *Proceedings of the 49th ASMA Conference on Mass Spectrometry and Allied Topics*, A010970, 2001.

Sharma et al., "Novel taxol formulations preparation and characterization of taxol-containing liposomes," *Pharm. Res.*, vol. 11, 1994, pp. 889-896 © Plenum Publishing Corp.

Shi, "Poly (L-glutamic acid)-paclitaxel and paclitaxel have different pharmacological properties," *Proc. Amer. Assoc. for Cancer Research*, vol. 39, 1998, p. 189, Abstract No. 1294.

Singer et al., "Conjugation of Camptothecins to Poly-(L-Glutamic Acid)," Annals of the New York Academy of Sciences, vol. 922, 2000, pp. 135-150, © The New York Academy of Sciences.

Singer et al., "Poly-L-Glutamic Acid Paclitaxel Conjugate (PG-TXL): A water-soluble biodegradable conjugate with decreased toxicity and enhanced efficacy," *4th International Symposium on Polymer Therapeutics*, 2000.

Todd et al., "Phase I and pharmacological Study of CT-2103, a poly (L-glutamic Acid)-paclitaxel conjugate," *Journal of Clinical Oncology*, vol. 439, 2001.

Van Heeswijk et al., The Synthesis and Characterization of Polypeptide-Adriamycin Conjugates and its Complexes with Adriamycin. Part 1, *Journal of Controlled Release*, vol. 1, 1985, pp. 301-315 © Elsevier Science Publishers B.V.

Vyas et al., "Phosphate-activated prodrugs of paclitaxel," *Taxane Anticancer Agents*, Chapter 9, 1995, pp. 124-137 © American Chemical Society.

Wadkins et al., Water Soluble 20-(S)-Glycinate Esters of 10,11-Methylenedioxycamptothecins Are Highly Active Against Human Breast Cancer Xenografts[1,] *Cancer Research*, vol. 59, pp. 3424-3428, 1999.

Wadkins et al., Water Soluble 20(S)-Glycinate Esters of 10,11-Methylenedioxycamptothecins Are Highly Active Against Human Breast Cancer Xenografts' *Cancer Research*, vol. 59, 1999, pp. 3424-3428.

Wall et al., "Plant Antitumor Agents. 30,[1a,b] Synthesis and Structure Activity of Novel Camptothecin Analogs," *Journal of Medicinal Chemistry*, vol. 36, 1993, pp. 2689-2700, © American Chemical Society.

Wang et al., "Recent Advances in the Discovery and Development of Topoisomerase Inhibitors as Antitumor Agents," *Medicinal Research Reviews*, vol. 17, No. 4, pp. 367-425, © John Wiley & Sons, Inc., 1997.

Weiss et al., "Hypersensitivity reactions from taxol," *J. Clin. Oncol.*, vol. 8, 1990, pp. 1263-1268 © American Society of Clinical Oncology.

Wen et al., "Potentiation of Antitumor Activity of PG-TXL with Anti-EGFR Monoclonal Antibody C225 in MDA-MB-468 Human Breast Cancer Xenograft," *Proc Am Assoc Cancer Res*, vol. 41, 2000, Abstract No. 2052.

Yang et al., "Application of surface-modified microcapsules to target estrogen receptors," *Pharm. Res.*, vol. 9, 1992, p. S73, Abstract No. Biotec 2027.

Yang et al., "Diagnostic and therapeutic potential of poly(benzyl L-glutamate)," *J. Pharm. Sci*, vol. 83, 1994, pp. 328-331 © American Chemical Society and American Pharmaceutical Association.

Yu, "Effect of polymer structure on antitumor activity of polyaminio acid-paclitaxel conjugates," *Proc. Amer. Assoc. Cancer Research*, vol. 39, 1998, p. 167, Abstract No. 1144.

Zhang et al., "An investigation of the antitumor activity and biodistribution of polymeric micellar paciltaxel," *Cancer Chemother. Pharmacol*, vol. 40, 1997, pp. 80-86 © Springer-Verlag.

Zhao et al., "Modified taxols. 6 preparation of water-soluble taxol phosphates," *J. Nat. Prod.*, vol. 54, 1991, pp. 1607-1611.

Zheng et al., "Deacetylation of Paclitaxel and Other Taxanes," *Tetrahedron Letters*, vol. 36, 1995, pp. 2001-2004, © Elsevier Science Ltd.

Zunino et al , "Anti-Tumor Activity of Daunorubicin Linked to Poly-L-Aspartic Acid," *Int. J. Cancer*, vol. 30, 1982, pp. 465-470.

* cited by examiner

1: R1 = R2 = H
2: R1 = OCOCH₃, R2 = H
3: R1 = OH, R2 = H

4: L = -NHCH₂CO-
5: L = -NHCH₂CO-NHCH₂CO-
6: L = -NHCH₂CO-NHCH₂CO-NHCH₂CO-
7: L = -(S)-NHCH(CH₃)CO-
8: L = -NHCH₂CH₂CO-
9: L = -NHCH₂CH₂CH₂CO-
10: L = -OCH₂CO-
11: L = -OCH₂CH₂CH₂CO-
12: L = -(S)-NHCH(CO₂H)CH₂CH₂CO-

13

14

15

16

17: R1 = OH, R2 = H
18: R1 = OH, R2 = CH₂CH₃
19: R1 = OCOCH₃, R2 = Si(CH₃)₂C(CH₃)₃

POLYGLUTAMIC ACID-CAMPTOTHECIN CONJUGATES AND METHODS OF PREPARATION

CROSS-REFERENCE TO RELATED APPLICATIONS

This is a Continuation Application of application Ser. No. 09/956,237, filed Sep. 20, 2001 now abandoned, which is in turn a Continuation-In-Part of application Ser. No. 09/810,345, filed Mar. 19, 2001 now abandoned, which claims benefit of Provisional Application No. 60/190,429, filed Mar. 17, 2000.

FIELD OF THE INVENTION

This invention relates to compositions comprising polyglutamic acid polymers that are covalently conjugated to camptothecin and biologically active camptothecin analogs, respectively. The invention also relates to the preparation and the pharmaceutical uses of such compositions.

BACKGROUND OF THE INVENTION

Camptothecin is a water insoluble, optically active alkaloid obtained from the *Camptotheca acuminata* tree. 20(S)-camptothecin and 20(S)-camptothecin analogs are cytotoxic agents that are thought to act by stabilizing a topoisomerase I-induced single strand break in the phosphodiester backbone of DNA, thereby preventing religation. This leads to the production of a double-strand DNA break during replication, which results in apoptosis if not repaired.

20(S)-camptothecin and many 20(S)-camptothecin analogs are water insoluble. Many of these drugs exhibit excellent antitumor activity against human cancer cell lines and in vivo animal xenografts. However, their water insolubility makes it difficult to administer these drugs. Additionally, the pharmacologically important lactone ring of 20(S)-camptothecin and its analogs is unstable in the presence of human plasma albumin which results in the conversion of the active drug to the inactive carboxylate form which is bound to the albumin.

One approach to overcome the pharmaceutical and pharmacokinetic shortcomings of 20(S)-camptothecin and 20(S)-camptothecin-analogs is to covalently bind them to neutral polymers such as polyethylene glycol (see, e.g., references 1 and 2 below); Using this approach, the water solubility of the most active camptothecins can be improved such that the conjugated polymers can be parenterally administered in aqueous medium.

There is a continuing need for new polymeric conjugates that are capable of solubilizing a greater amount of 20(S)-camptothecin or 20(S)-camptothecin analog per polymer chain to decrease the total mass of polymer needed for administering a given dose of the active drug. As well, there is a continuing need for new polymeric conjugates that may have unique properties as antitumor agents that are not found in unconjugated water-soluble prodrugs and analogs of 20(S)-camptothecin.

Background Publication
1. U.S. Pat. No. 5,646,159
2. Greenwald et al., *Bioorg. Med. Chem.* 6:551–562 (1998)
3. U.S. Pat. No. 5,545,880
4. Conover et al. *Cancer Chemother. Pharmacol.* 42:407–414 (1998)
5. PCT Application WO99/17804
6. Hesswijk et al. *J. Cont. Re.* 1:312 (1985)
7. U.S. Pat. No. 5,880,131
8. U.S. Pat. No. 5,892,043
9. U.S. Pat. No. 5,837,673
10. U.S. Pat. No. 5,854,006
11. U.S. Pat. No. 5,340,817
12. U.S. Pat. No. 4,943,579
13. Singer et al., *Ann. NY Acad. Sci.* 922:136–150 (2000)

DETAILED DESCRIPTION OF THE INVENTION

Definitions

Figure 1:
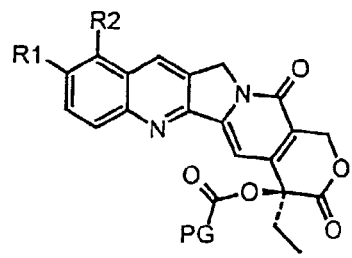
FIG. 1 shows the structures for the PG-camptothecin (PG-CPT) conjugates enumerated in Table 1.
Figure 1:
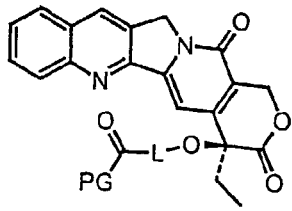
Figure 1:
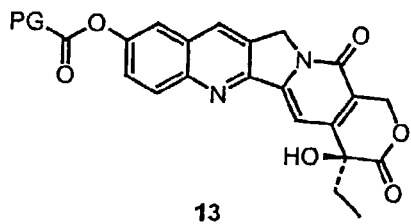
Figure 1:
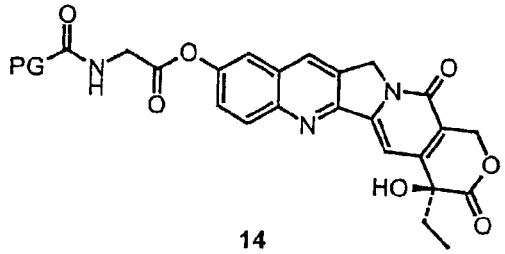
Figure 1:
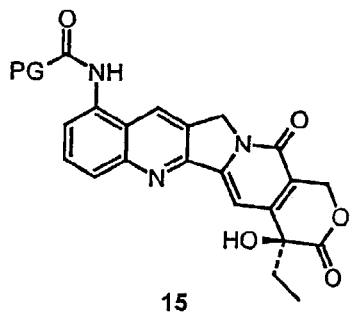
Figure 1:
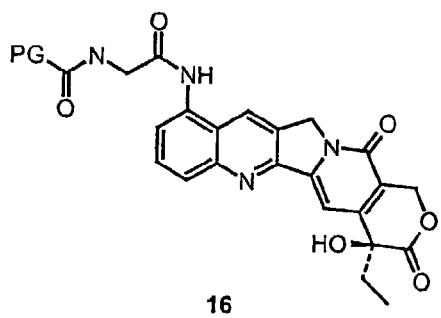
Figure 1:
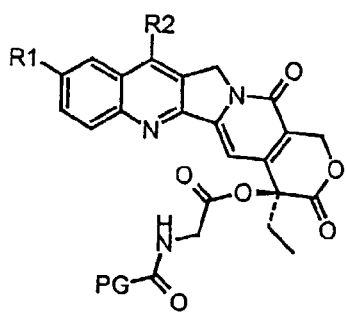

As used herein, "a polyglutamic acid" or "polyglutamic acid polymer" includes poly (l-glutamic acid), poly (d-glutamic acid), poly (dl-glutamic acid), poly (l-gamma glutamic acid), poly (d-gamma glutamic acid) and poly (dl-gamma glutamic acid). Preferably the polyglutamic acid polymer comprises at least 50% of its amino acid residues as glutamic acid, and more preferably, 100%. The polyglutamic acid polymer can be substituted up to 50% by naturally occurring or chemically modified amino acids, preferably hydrophilic amino acids, provided that when conjugated to a therapeutic agent, the substituted polyglutamic acid polymer has improved aqueous solubility and/or improved efficacy relative to the unconjugated therapeutic agent, and is preferably nonimmunogenic.

The molecular weight of the polyglutamic acid polymer used in the preparation of the conjugate by the methods described herein is typically greater than 5000 daltons, preferably from 20 kD to 80 kD, more preferably from 25 kD to 60 kD (as determined by viscosity). Those skilled in the art will appreciate that the molecular weight values may be different when measured by other methods. These other methods include, for example, gel permeation, low angle light scattering, multiple angle laser light scattering, refractive index and combinations thereof.

As used here, "PG" refers to polyglutamic acid polymer.

As used herein, "camptothecin" refers to 20(S)-camptothecin or a biologically active 20(S)-camptothecin analog. "CPT" refers to 20(S)-camptothecin, having the structure shown below:

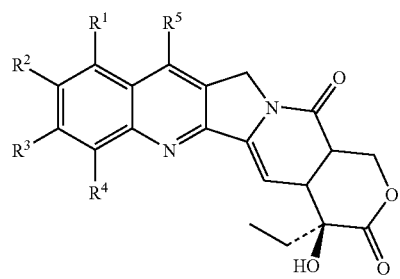

where $R^1=R^2=R^3=R^4=R^5=H$.

"20(S)-camptothecin analog" refers to a biologically active 20(S)-camptothecin analog where one or more R groups on the camptothecin structure shown above are other than H. See, e.g., Wang et al. *Med. Res. Rev.* 17:367–425 (1997); Labergne and Bigg *Bull. Cancer (Paris)* 1: 51–8 (1998); and Table 2 herein.

As used herein, the term "polyglutamic acid-camptothecin conjugate" or "PG-camptothecin" refers to a polyglutamic acid polymer that is covalently bonded to 20(S)-camptothecin or a biologically active 20(S)-camptothecin analog by a direct linkage between a carboxylic acid group of the polyglutamic acid and a functional group of the therapeutic agent, or by an indirect linkage via a bifunctional spacer group. Preferred spacer groups are those that are relatively stable to hydrolysis in the circulation, are biodegradable and are nontoxic when cleaved from the conjugate. It is understood that suitable spacers will not interfere with the antitumor efficacy of the conjugates. Exemplary spacers include amino acids (e.g., glycine, alanine, β-alanine, glutamic acid, leucine, isoleucine), —[NH—(CHR')$_p$—CO]$_n$—, wherein R' is a side chain of a naturally occurring amino acid, n is an integer between 1 and 10, most preferably between 1 and 3; and p is an integer between 1 and 10, most preferably between 1 and 3; hydroxyacids of the general formula —[O—(CHR')$_p$—CO]$_n$—, wherein R' is a side chain of a naturally occurring amino acid, n is an integer between 1 and 10, most preferably between 1 and 3; and p is an integer between 1 and 10, most preferably between 1 and 3 (e.g., 2-hydroxyacetic acid, 4-hydroxybutyric acid); diols, aminothiols, hydroxythiols, aminoalcohols, and combinations of these. Presently preferred spacers are amino acids, more preferably naturally occurring amino acids, more preferably glycine. A therapeutic agent can be linked to the polymer or spacer by any linking method that results in a physiologically cleavable bond (i.e., a bond that is cleavable by enzymatic or nonenzymatic mechanisms that pertain to conditions in a living animal organism). Examples of preferred linkages include ester, amide, carbamate, carbonate, acyloxyalkylether, acyloxyalkylthioether, acyloxyalkylester, acyloxyalkylamide, acyloxyalkoxycarbonyl, acyloxyalkylamine, acyloxyalkylamide, acyloxyalkylcarbamate, acyloxyalkylsulfonamide, ketal, acetal, disulfide, thioester, N-acylamide, alkoxycarbonyloxyalkyl, urea, and N-sulfonylimidate. Most preferred at present are amide and ester linkages.

Methods for forming these linkages are well known to those skilled in synthetic organic chemistry, and can be found for example in standard texts such as March, *Advanced. Organic Chemistry*, Wiley Interscience (1992).

The degree of loading of camptothecin on the PG may be expressed as the number of molecules per polyglutamic acid polymer chain or preferably as a % of total weight of the conjugate ("% loading"). The optimal degree of loading for a given conjugate and given use is determined empirically based on the desired properties of the conjugate (e.g., water solubility, therapeutic efficacy, pharmacokinetic properties, toxicity and dosage requirements). In preferred embodiments, the % loading is 10–50%, 15–50%, 25–50%, 27–40%, 30–50%, 30–47%, 30–45%, 30–40%, 30–37%, 30–35%, 35–47%, 35–45%, 35–40%, 35–39%, and 35–37%. The % loading of PG-camptothecin conjugates can be measured as described below under Methods of Preparation.

Generally, the camptothecin or camptothecin analog is capable of attachment to the polymer by means of a functional group that is already present in the native molecule or otherwise can be introduced by well-known procedures in synthetic organic chemistry without altering the activity of the agent. In the examples given herein, and as shown in Table 3, the camptothecin is relatively water-insoluble in the unconjugated form and shows greatly improved solubility following conjugation. However, even water-soluble analogs and prodrugs (e.g., amino acid esters) are expected to show advantages following their conjugation to polyglutamic acid (e.g., improved pharmacokinetics and retention at the site of action compared to the unconjugated agent, enhanced efficacy).

Reactions performed under "standard coupling conditions" are carried out in an inert solvent (e.g., dimethylformamide, dimethysulfoxide, N-methylpyrrolidone) at a temperature from –20° C. to 150° C., preferably from 0° C. to 70° C., more preferably from 0° C. to 30° C., in the presence of a coupling reagent and a catalyst. Of course, the temperature used will depend on factors such as the stability of the therapeutic agent and the reactivity of the attaching group. Suitable coupling reagents are well-known in synthetic organic chemistry and include, but are not limited to, carbodiimides, alkyl chloroformate and triethylamine, pyridinium salts-tributyl amine, phenyl dichlorophosphate, 2-choro-1,3,5-trinitrobenzene and pyridine, di-2-pyridyl carbonate, polystyryl diphenylphosphine, (trimethylsilyl) ethoxyacetylene, 1,1'-carbonylbis(3-methylimidazolium)triflate, diethylazodicarboxylate and triphenyl phosphine, N,N' carbonyldiimidazole, methanesulphonyl chloride, pivaloyl chloride, and the like. Suitable catalysts for alcohol coupling include, e.g., 4-N,N dimethylaminopyridine and 4-pyrollidinopyridine.

As used herein, the term "inert solvent" means a solvent inert under the conditions of the reaction being described in conjunction therewith [including, for example, benzene, toluene, acetonitrile, tetrahydrofuran ("THF"), dimethylformamide ("DMF"), chloroform ("CHCl$_3$"), methylene chloride (or dichloromethane or "CH$_2$Cl$_2$"), diethyl ether, ethyl acetate, acetone, methylethyl ketone, dioxane, pyridine, dimethoxyethane, t-butyl methyl ether, and the like. Unless specified to the contrary, the solvents used in the reactions of the present invention are inert solvents.

If multiple functional groups are present on the camptothecin, selective attachment of a particular functional group to the polyglutamic acid polymer will typically require the use of a suitable protecting group. The term "protecting group" or "blocking group" refers to any group which when bound to one or more hydroxyl, thiol, amino or carboxyl groups of the compounds prevents reactions from occurring at these groups and which protecting group can be removed by conventional chemical or enzymatic steps to reestablish the hydroxyl, thiol, amino or carboxyl group. Generally, see Greene and Wuts PROTECTIVE GROUPS IN ORGANIC SYNTHESIS, 1999 (John Wiley and Sons, N.Y.).

The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl, t-butyldimethylsilyl, triethylsilyl, MOM (methoxymethyl), MEM (2 -methoxyethoxy methyl) and any other group that can be introduced chemically onto a hydroxyl functionality and later selectively removed either by chemical or enzymatic methods in mild conditions compatible with the nature of the product.

Preferred removable amino blocking groups include conventional substituents such as t-butyoxycarbonyl (t-BOC), benzyloxycarbonyl (CBz), fluorenylmethoxycarbonyl (FMOC), allyloxycarbonyl (ALOC), trichloroethoxycarbonyl (TROC) and the like, which can be removed by conventional conditions compatible with the nature of the product.

Preferred carboxyl protecting groups include esters such as methyl, ethyl, propyl, t-butyl etc. which can be removed by mild hydrolysis conditions compatible with the nature of the product.

Nomenclature

The PG-camptothecin conjugates of the present invention are named as shown for exemplary conjugates in Table 1. The nomencluature used in Table 1 also can be understood by referring to FIG. 1.

TABLE 1

| Compound | PG Conjugate |
|---|---|
| 1 | PG-CPT (20-conjugated) |
| 2 | PG-(10-OAc-CPT) (20-conjugated) |
| 3 | PG-(10-OH-CPT) (20-conjugated) |
| 4 | PG-gly-CPT (20-linked) |
| 5 | PG-gly-gly-CPT (20-linked) |
| 6 | PG-gly-gly-gly-CPT (20-linked) |
| 7 | PG-ala-CPT (20-linked) |
| 8 | PG-(β-ala)-CPT (20-linked) |
| 9 | PG-(4-NH-butyryl)-CPT (20-linked) |
| 10 | PG-(2-O-acetyl)-CPT (20-linked) |
| 11 | PG-(4-O-butyryl)-CPT (20-linked) |
| 12 | PG-(γ-glu)-CPT (20-linked) |
| 13 | PG-(10-O-CPT) (10-conjugated) |
| 14 | PG-gly-(10-O-CPT) (10-linked) |
| 15 | PG-(9-NH-CPT) (9-conjugated) |
| 16 | PG-gly-(9-NH-CPT) (9-linked) |
| 17 | PG-gly-(10-OH-CPT) (20-linked) |
| 18 | PG-gly-(7-Et-10-OH-CPT) (20-linked) |
| 19 | PG-gly-(7-t-BuMe$_2$Si-10-OAc-CPT) (20-linked) |

DESCRIPTION OF THE PREFERRED EMBODIMENTS

A. Conjugates

The present invention encompasses pharmaceutically active polyglutamic acid-camptothecin conjugates, which are characterized by the general formula I:

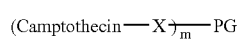

wherein:

PG is polyglutamic acid polymer;

X is a single bond, an amino acyl linker —[OC—(CHR')$_p$—NH]$_n$—, or a hydroxyacyl linker —[OC—(CHR')$_p$—O]$_n$—, where R' is a side chain of a naturally occurring amino acid;

Camptothecin is 20(S)-camptothecin or a biologically active 20(S)-camptothecin analog;

m is a positive integer of 5 to 65;

Camptothecin-X is covalently linked to a carboxyl group of said polymer through an ester or amide linkage;

n is an integer between 1 and 10, most preferably between 1 and 3; and p is an integer between 1 and 10, most preferably between 1 and 3;

and the specific formulas II–VII:

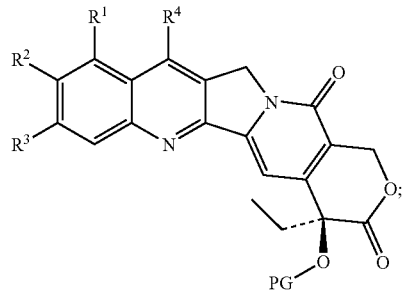

where R$^1$, R$^2$, R$^3$ and R$^4$ are each H; or
R$^1$ is —NH$_2$, and R$^2$, R$^3$ and R$^4$ are each H; or
R$^1$ is —NO$_2$, and R$^2$, R$^3$ and R$^4$ are each H; or
R$^1$, R$^3$ and R$^4$ are each H and R$^2$ is —OH; or
R$^1$, R$^3$ and R$^4$ are each H and R$^2$ is —O—C(O)—CH$_3$; or
R$^1$ and R$^3$ are each H, R$^4$ is —SiMe$_2$t-Bu and R$^2$ is —OH.

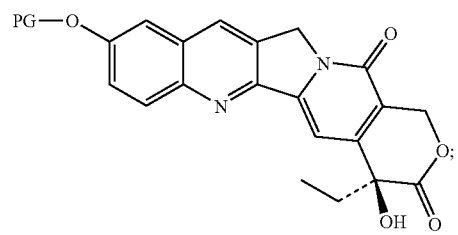

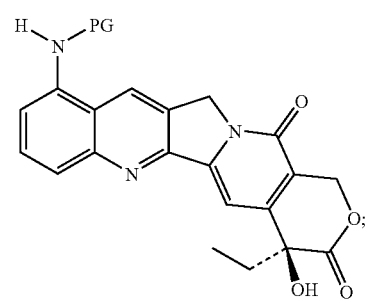

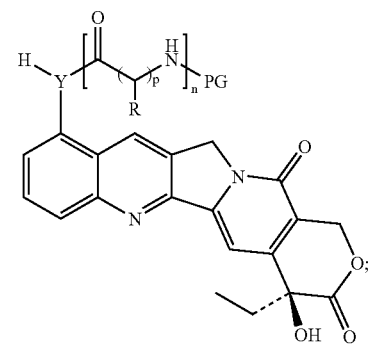

wherein Y is N or O;

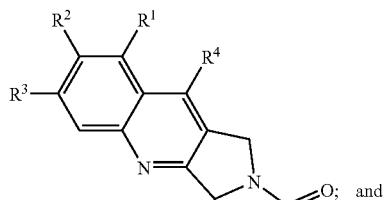

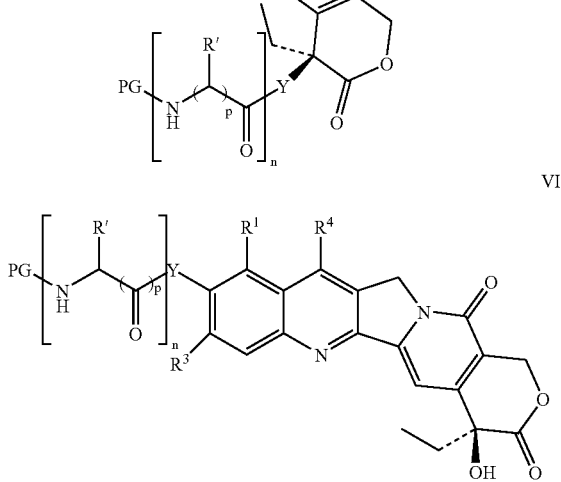

wherein:
Y is N or O;
R' is a side chain of a naturally occurring amino acid;
$R^1$ is —$NH_2$ or H;
$R^2$ is —H, —OH, or —O—C(O)—$CH_3$;
$R^3$ is —H or alkyl; and
$R^4$ is —H, alkyl, or trialkylsilyl.

As used herein, the term "alkyl" refers to an aliphatic hydrocarbon group. The alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). More preferably, it is a "medium" size alkyl having 1 to 10 carbon atoms. Most preferably, it is a "lower" alkyl having 1 to 4 carbon atoms e.g., methyl, ethyl, propyl, isopropyl, n-butyl, tert-butyl, iso-butyl. The alkyl group may be substituted or unsubstituted. When substituted, the substituent group(s) is(are) preferably one or more group(s) individually and independently selected from hydroxy, alkoxy, mercapto, alkylthio, cyano, halo, carbonyl, nitro, and amino.

As used herein, the term "trialkylsily" refers to the group —Si(alkyl)$_3$, wherein the term "alkyl" is defined above.

The preferred embodiments of this invention comprise PG-camptothecin conjugates that exhibit significant antitumor activity, enhanced aqueous solubility, reduced toxicity and increased maximum tolerated doses (MTD) compared with the unconjugated camptothecin or camptothecin analog. These conjugates are also expected to exhibit unique pharmacokinetic properties (e.g., enhanced permeability and retention in tumor tissue, sustained release of active agent, long biological half life) compared with the unconjugated agent and to stabilize the lactone ring form of the drugs, which is known to be critical for their activity. Additionally, it is expected that the ability to solubilize highly insoluble camptothecin analogs by conjugation to multiple available conjugation sites on PG will extend the range of clinically useful camptothecin analogs that may be highly active but which cannot presently be used because of their solubility problems.

With reference to the above formulae, PG-camptothecin conjugates represented by formula II and formula VI are presently most preferred, where:
R', $R^1$, $R^2$, $R^3$ and $R^4$ are each H;
$R^1$, $R^3$ and $R^4$ are each H and $R^2$ is —OH or —O—C(O)—$CH_3$;
$R^1$ is —$NH_2$, and $R^2$, $R^3$ and $R^4$ are each H;
and the conjugate represented by formula IV.

The polyglutamic acid polymer used in the conjugate should be water soluble, biodegradable and substantially nonimmunogenic. The polyglutamic acid polymers that are encompassed in the scope of this invention are described above (see Definitions). The molecular weight of the polyglutamic acid polymer is typically greater than 5000 daltons, preferably from 20 kD to 80 kD, more preferably from 25 kD to 60 kD (as determined by viscosity). Most preferred at present are poly-(L-glutamic acid) polymers having a molecular weight of between 30 kD and 50 kD. Those skilled in the art will appreciate that the molecular weight values may be different when measured by other methods. These other methods include, for example, gel permeation, low angle light scattering, multiple angle laser light scattering, refractive index and combinations thereof.

For the direct conjugates of the invention, the % loading preferably ranges from about 7% to about 20%, more preferably from about 10% to about 17%, and even more preferably, from about 12% to about 15%. For conjugates linked indirectly to PG via an amino acid linker, the % loading preferably ranges from about 7% to about 50%, preferably from about 15% to about 38%, most preferably from about 20% to about 38%.

B. Methods of Preparation

The polyglutamic acid-camptothecin conjugates of the present invention are prepared by direct or indirect linkage of a biologically active camptothecin compound to a polyglutamic acid polymer. Any camptothecin compound may be used provided that it contains or can be functionalized with a group that can be linked to a gamma-carboxylate group of PG, preferably through an ester or amide linkage. See, e.g., Wang et al. *Med. Res. Rev.* 17:367–425 (1997), Labergne and Bigg, *Bull. Cancer (Paris)* 1: 51–8 (1998), and Table 2 below.

Thus 20(S)-camptothecin and biologically active 20(S)-camptothecin analogs can be linked to PG through the 20(S)-hydroxyl group of the camptothecin nucleus, or through another available functional group of an analog.

In general, the directly linked polyglutamic acid-camptothecin conjugates are prepared by dissolving the camptothecin and polyglutamic acid in dimethylformamide or other inert solvent, cooling the solution and adding to the cooled mixture a coupling reagent and an excess of an amine base, e.g., dimethylaminopyridine. Surprisingly, it has now been discovered that the use of bis(2-oxo-3-oxazolidinyl) phosphinic chloride (BOP-Cl) or 2-chloromethylpyridinium iodide as coupling reagents enables the preparation of conjugates with significantly increased content of 20(S)-camptothecin or a 20(S)-camptothecin analog (i.e., % loading in the range of about 10%–20%), compared with what was previously known in the art. This finding is particularly important because it provides compositions with a greatly increased molar ratio of active drug to PG polymer and thereby decreases the total mass of polymer needed to administer a given dose of drug to a patient. Other advantageous and novel features of these conjugates are discussed elsewhere in this application.

The reaction mixture is allowed to warm and is stirred for sufficient time for the reaction to proceed to about 70% completion. The resultant conjugate may be isolated by precipitating it from solution by addition of an excess volume of an aqueous salt solution (e.g., NaCl, KCl, $NH_4Cl$), preferably 10–15% salt solution, with cooling of the reaction mixture between 0° C. and 10° C. and collecting the conjugate as a solid in its protonated form.

It has been found that the removal of unreacted camptothecin from the conjugate is necessary to ensure a high degree of efficacy of the compositions of the invention with minimal toxicity. Unreacted camptothecin and other impurities may be extracted by washing the solid conjugate with an organic solvent in which unreacted camptothecin and other impurities (but not the conjugate) are soluble, e.g., 1 to 3% methanol-dichlbromethane, 1 to 3% methanol-chloroform, chloroform, dichloroethane, and others. In general, the presence of unreacted camptothecin in the conjugate product can be detected by sonicating the conjugate for 3 hours in 2% methanol-dichloromethane and analyzing for camptothecin in the organic extract by thin layer chromatography (TLC). The $^1H$ NMR spectrum of the conjugate provides confirmation that the camptothecin is covalently bound to PG (see Table 3 for NMR analyses of selected exemplary conjugates).

To determine the amount of drug loaded on the polymer, a portion of the directly conjugated PG-camptothecin is subjected to hydrolysis with base to release the conjugated camptothecin, which also opens the lactone ring to the free carboxylic acid salt. Following acidification to reclose the carboxylate to the lactone, the released camptothecin is extracted. The camptothecin thus obtained is compared to an authentic sample of the camptothecin by thin layer chromatography (TLC) and $^1H$ NMR. The % loading is calculated from the amount of camptothecin that is recovered in the extract and the weight of the product conjugate. The % loading can also be determined by measuring the UV absorbance of PG-camptothecin and calculating the camptothecin content from a camptothecin standard curve. Typically, this determination is performed at 364 nm. One of ordinary skill in the art, however, can determine the optimal wavelength for this determination with only routine experimentation.

When multiple functional groups are available for attachment, the selective attachment of a particular group of the drug to the polyglutamic acid polymer may require the use of a suitable protecting group depending on the differential reactivities of the groups. A non-limiting example of a suitable protecting group is the acetyl group. Other suitable protecting groups known to the skilled artisan are described, for example, in Greene and Wuts PROTECTIVE GROUPS IN ORGANIC SYNTHESIS, 1999 (John Wiley and Sons, N.Y.).

Treatment of 20(S)-10-hydroxycamptothecin with an active acyl donor such as acetic anhydride in the presence of pyridine base gave reaction exclusively at the 10-hydroxyl group. The 10-acetoxy derivative was then linked to PG through the 20(S)-hydroxyl. Acetate was chosen as a blocking group because it is expected to be hydrolyzed in vivo and pharmaceutically acceptable. Alternatively, the 10-hydroxyl group can be blocked by a removable protecting group (e.g., BOC) prior to conjugation to PG, then unblocked with trifluoroacetic acid treatment (see Example 3 below). In the absence of a blocking group, reaction of 20(S)-10-hydroxycamptothecin with PG using chloromethylpyridinium iodide/4-dimethylaminopyridine/PG-H in dimethylformamide afforded PG-(10-O-CPT) as the exclusive product.

Coupling of 20(S)-9-aminocamptothecin to PG under conditions of direct conjugation (chloromethylpyridinium iodide and 4-dimethylaminopyridine) took place on the aromatic A-ring heteroatom substituent in this case producing PG-9-NH-CPT as the exclusive product. This outcome was inferred based upon results of an analogous coupling of 20(S)-9-aminocamptothecin with Boc-L-glutamic acid α-tert-butyl ester that afforded a product whose $^1H$ NMR spectrum displayed characteristic shifts of signals due to the 20(S)-9-aminocamptothecin aromatic protons while signals due to lactone ethyl protons were not shifted.

The PG-camptothecin conjugates encompassed by this invention can also be prepared by inserting a bifunctional linker between the 20(S)-camptothecin or 20(S)-camptothecin analog and the alpha or gamma carboxy group of the PG polymer. Preferred linkers are naturally occurring amino acids, β-amino acids, gamma amino acids or hydroxyacids, more preferably glycine linkers. The use of linkers provides efficacious conjugates with an even greater % loading of 20(S)-camptothecin and its analogs than for direct conjugates.

The indirect conjugates are generally prepared by preparing an amino acid ester or hydroxy ester of 20(S)-camptothecin or a desired 20(S)-camptothecin analog according to known procedures (see, e.g., U.S. Pat. No. 5,646,159 and Greenwald et al., *Bioorg. Med. Chem.* 6:551–562 (1998), to a alpha or gamma carboxy group of PG through an amino group of the amino acid or the hydroxy group of a hydroxyacid under standard coupling conditions to form an amide or ester linkage, respectively.

Conjugation of 20(S)-10-hydroxycamptothecin to PG through a glycine linker attached to the 20(S)-hydroxyl group was accomplished by treating 20(S)-10-hydroxycamptothecin with di-tert-butyl dicarbonate and pyridine to provide exclusively the corresponding 10-O-Boc derivative. The latter was 20-O-acylated with Boc-glycine using a carbodiimide coupling reagent (e.g., diisopropylcarbodiimide, 1-ethyl-3-(3-dimethylaminopropyl)carbodiimide) and 4-dimethylaminopyridine. Removal of both Boc protecting groups with trifluoroacetic acid followed by conjugation with PG provided PG-gly-(10-OH-CPT). PG-gly-(7-Et-10-OH-CPT) and PG-gly-(7-t-BuMe$_2$Si-10-OAc-CPT) were synthesized using this method.

Conjugation of 20(S)-10-hydroxycamptothecin to PG through a glycine linker attached to the 10-hydroxyl group is carried out as follows. Treatment of 20(S)-10-hydroxycamptothecin with the symmetrical anhydride of Boc-glycine and pyridine yielded only the corresponding 10-(N-Boc)-glycinate ester. Treatment of the latter with trifluoroacetic acid effected cleavage of the N-Boc protecting group. The resulting 10-glycinate ester of 20(S)-10-hydroxycamptothecin was conjugated with PG using 1,3-diisopropylcarbodiimide and 4-dimethylaminopyridine to give PG-gly-(10-O-CPT)).

Exclusive coupling to the α-amino group of the glycine was inferred based on an analogous coupling of the 10-glycinate ester of 20(S)-10-hydroxycamptothecin with N-Boc-L-glutamic acid α-tert-butyl ester under the same reaction conditions. The $^1H$ NMR spectrum of this reaction product displayed characteristic shifts of signals due to 20(S)-10- hydroxycamptothecin aromatic protons whereas signals due to lactone ethyl group protons were not shifted.

The first two steps of the conjugation of 20(S)-9-aminocamptothecin to PG through a glycine linker attached to the 9-amino group may be accomplished by the method described by Wall et al., *J. Med. Chem.* 36: 2689–2700 (1993). The conjugation of 20(S)-9-(glycylamino)camptothecin trifluoroacetic acid salt to PG was carried out in the presence of diisopropylcarbodiimide and dimethylaminopyridine to provide PG-gly-(9-NH-CPT).

Conjugation of PG to 20(S)-camptothecin using a glycyl-glycine (gly-gly; di-gly) linker was accomplished by first reacting 20-O-(glycyl)camptothecin trifluoroacetic acid salt with N-(tert-butoxycarbonyl)glycine in the presence of a carbodiimide coupling reagent to provide 20-O-((N-(tert-butoxycarbonyl)glycyl)glycyl)camptothecin. The latter was then treated with trifluoroacetic acid to give 20-O-(glycyl-glycyl)camptothecin trifluoroacetic acid salt. 20-O-(glycyl-glycyl)camptothecin trifluoroacetic acid salt was then reacted with poly-L-glutamic acid in the presence of N,N-dimethylaminopyridine and 1,3-diisopropylcarbodiimide to provide PG-gly-gly-CPT.

Conjugation of PG to 20(S)-camptothecin using a glycyl-glycyl-glycine (gly-gly-gly; tri-gly) linker was accomplished by reacting ((N-(tert-butoxycarbonyl)glycyl)glycyl) glycine and 20(S)-camptothecin in the presence of N,N-dimethylaminopyridine and 1,3-Diisopropylcarbodiimide to provide 20-O-(((N-(tert-butoxy-carbonyl)glycyl)glycyl)glycyl)camptothecin. 20-O-(((N-(tert-butoxycarbonyl)glycyl)-glycyl)glycyl)camptothecin was then treated with trifluoroacetic acid to yield 20-O-(glycyl-glycyl-glycyl)camptothecin trifluoroacetic acid salt. The latter was reacted with poly-(L-glutamic acid) (956 mg) in the presence of N,N-dimethylaminopyridine and 1,3-diisopropylcarbodiimide to yield PG-gly-gly-gly-CPT.

The PG-camptothecin conjugates of the present invention exhibit antitumor activity against various tumors including human lung cancer, human non-small cell lung cancer, breast cancer, ovarian cancer and melanoma (see Example 20). It is believed that these conjugates will be active against a broad spectrum of mammalian (including human) cancers, including solid tumors (e.g., lung, ovarian cancer, breast, gastrointestinal, colon, pancreas, bladder, kidney, prostate, brain) and various hematopoietic cancers (e.g., Hodgkin's disease, non-Hodgkin's lymphoma, leukemias). It is believed that these conjugates may also be useful in treating drug-resistant cancers.

Pharmaceutical compositions containing the PG-camptothecin conjugates of the present invention are included in the scope of the invention. These pharmaceutical compositions may contain any quantity of conjugate that is effective in exhibiting antitumor activity in vivo. Clinicians of ordinary skill in the art of medicine will know that the dosage that is administered to a patient will vary according to the age, weight and physical condition of the patient, the route of administration, the specific cancer being treated, the stage of tumor development and the like. For any particular subject, the specific dosage regimens (both dosage and frequency of administration) should be adjusted for that patient by a skilled practitioner. Doses that are contemplated to be effective for in vivo administration of the conjugates (preferably by parenteral or intravenous administration) are in the range of about 0.1–100 mg eq. camptothecin or camptothecin analog per kg body weight per day, preferably from 1–60 mg eq. camptothecin or camptothecin analog per kg body weight per day.

The pharmaceutical compositions comprise a pharmaceutically effective amount of PG-camptothecin conjugate in a pharmaceutically acceptable carrier or diluent. Determination of the effective amount of a pharmaceutical composition is well within the capability of those skilled in the art. Acceptable carriers or diluents for therapeutic use are well known in the pharmaceutical art, and are described, for example, in REMINGTON'S PHARMACEUTICAL SCIENCES, Mack Publishing Co. (A. R. Gennaro edit. 1985). Preservatives, stabilizers, dyes and other agents may be provided in the pharmaceutical composition. It is within the scope of this invention to administer PG-camptothecin conjugates in combination therapy with other drugs, including but not limited to other antitumor drugs, and with radiation.

Depending on the specific conditions being treated, such pharmaceutical compositions may be formulated and administered systemically or locally. Techniques for formulation and administration may be found in REMINGTON'S PHARMACEUTICAL SCIENCES, supra. Suitable routes may include oral, rectal, transdermal, vaginal, transmucosal or intestinal administration; parenteral delivery, including intramuscular, subcutaneous, intramedullary injections, as well as intrathecal, direct intraventricular, intravenous, intraperitoneal, intranasal or intraocular injections.

For injection, the pharmaceutical compositions of the invention may be formulated in aqueous solutions, preferably in physiologically compatible buffers such as physiological saline buffer. Use of pharmaceutically acceptable carriers to formulate the pharmaceutical compositions herein disclosed for the practice of the invention in unit dosages suitable for systemic administration is within the scope of the invention.

The invention is illustrated by the following examples which should not be regarded as limiting the scope of the invention in any way.

EXAMPLES

In the following examples, the molecular weights of the polyglutamic acid used to prepare the conjugates are those specified by the supplier (Sigma), based on viscosity measurements. Further, the example number corresponds to the compound number in FIG. 1.

Example 1

PG-CPT (Method 1)

To a mixture of 20(S)-camptothecin (132 mg, 0.38 mmol) and poly-(L-glutamic acid) (33 kD, 530 mg), previously dried under vacuum for 4 hours, was added anhydrous dimethylformamide (20 ml). The solution was cooled in an ice bath and bis(2-oxo-3-oxazolidinyl)phosphinic chloride (174 mg, 0.68 mmol), N,N-dimethylaminopyridine (167 mg, 1.37 mmol) and diisopropylethylamine (74 mg, 0.57 mmol) were added. The reaction mixture was allowed to warm to room temperature. After stirring for 2 days the mixture was cooled in an ice bath and 10% aqueous sodium chloride solution (45 ml) was added over 25 min. This mixture was acidified to pH 2.5 by addition of 0.5 M hydrochloric acid (3.5 ml) and stirred at room temperature for 1 hour. The precipitate was filtered, washed with water (4×50 ml), and dried under vacuum for 12 hours. The solid was ground to a powder and suspended in 2% methanol-dichloromethane (10 ml). After stirring for 3 hours, the solid was separated by centrifugation and the supernatant decanted. This washing process was repeated 4 times to effect complete removal of unreacted camptothecin. The solid was dried under vacuum for 2 days, to yield PG-CPT (521 mg, 87% mass balance based on weight of recovered 20(S)-camptothecin (64.5 mg)). $^1$H NMR (300 MHz in DMSO-d$_6$): δ 12.10 (s, —COOH), 6.90–8.80 (m), 5.15–5.8 (m), 3.10–4.35 (m), 1.42–2.62 (m,), 0.90 (br s, 19-CH3).

The % weight loading of 20(S)-camptothecin in this sample of PG-CPT was determined as follows. To a suspension of PG-CPT (100 mg) in methanol-water (1:1, 4 ml) was added 1 M aqueous sodium hydroxide solution (2 ml). The yellow solution was stirred for 16 hours, acidified to pH 5 by addition of 1 M hydrochloric acid, and extracted with dichloromethane (4×20 ml). The, combined organic extracts were dried over magnesium sulfate and concentrated under reduced pressure to yield 20(S)-camptothecin (13 mg). The proton NMR and TLC of this sample were identical to that of an authentic sample of 20(S)-camptothecin. Based on these results, the % weight loading of 20(S)-camptothecin in this sample of PG-CPT was 13%.

PG-CPT (Method 2)

To a mixture of 20(S)-camptothecin (64 mg, 0.18 mmol) and poly-(L-glutamic acid) (50 kD, 256 mg), dried under vacuum for 6 hours, was added anhydrous dimethylformamide (15 ml). After cooling the solution to −5° C. in an ice/salt bath, 2-chloromethylpyridinium iodide (85 mg, 0.33 mmol) and N,N-dimethylaminopyridine (81 mg, 0.66 mmol) were added under an atmosphere of argon. The reaction mixture was allowed to warm to room temperature. After stirring for 4 days, the mixture was cooled to 0° C. and 10% aqueous sodium chloride solution (35 ml) was added over 25 minutes. The mixture was acidified to pH 2.5 by addition of 0.5 M hydrochloric acid (3.5 ml) and stirred at room temperature for 1 hour. The precipitate was filtered, washed with water (4×30 ml), and dried under vacuum. The solid was ground to a powder and suspended in 2% methanol-dichloromethane (10 ml). After stirring for 3 hours, the solid was separated by centrifugation and the supernatant decanted. This washing process was repeated 4 times to effect complete removal of unreacted camptothecin. The solid was dried under vacuum to yield PG-CPT (295 mg, 97% mass balance based on the weight of recovered 20(S)-camptothecin (13 mg)). $^1$H NMR (300 MHz in DMSO-d$_6$): δ 12.10 (s, —COOH), 6.90–8.80 (m), 5.15–5.8 (m), 3.10–4.35 (m), 1.42–2.62 (m), 0.90(br s, 19-CH$_3$).

The % weight loading of 20(S)-camptothecin in this sample of PG-CPT was determined to be 16% using the method described above in the synthesis of PG-CPT by Method 1.

Example 2

PG-(10-OAc-CPT)

20(S)-10-acetoxycamptothecin was prepared according to the method described in U.S. Pat. No. 4,545,880 (Miyasaka et al), which is hereby incorporated by reference in its entirety.

A suspension of poly-(L-glutamic acid) (50 kD, 235 mg) and 10-acetoxycamptothecin (53 mg, 0.13 mmol) in dimethylformamide (8 ml) was dissolved with gentle warming. When the resulting solution had cooled to room temperature, a solution of chloromethylpyridinium iodide (75 mg, 0.29 mmol) in dimethylformamide (2 ml) and a solution of 4-dimethylaminopyridine (73 mg, 0.60 mmol) in dimethylformamide (2 ml) were added sequentially. After stirring for 18 hours, the mixture was cooled in an ice bath and 10% aqueous sodium chloride solution (30 ml) was added over 30 minutes with vigorous stirring. After acidifying to pH 1–2 by slow addition of 0.5 M hydrochloric acid, the mixture was allowed to warm to room temperature and stirred for an additional 30 minutes. The solid was collected by centrifugation and the supernatant decanted. The solid was suspended in water (200 ml) and again isolated following centrifugation. This washing process was repeated 2 times and the solid was dried under vacuum. A suspension of the solid in 2% methanol-chloroform (25 ml) was treated with ultrasound for 90 minutes and filtered. This washing process was repeated and the solid was dried under vacuum to give PG-(10-OAc-CPT) (174 mg, 61% mass balance) as a yellow powder. $^1$H NMR (300 MHz. d$_6$-DMSO) δ 7.2–8.5 (multiple broad signals, Ar—H), 5.45, 5.20(br,s C-17, C-5 CH$_2$), 0.85(br triplet, C-18 CH$_3$), Example 3

PG-(10-OH-CPT)

To a solution of 20(S)-10-hydroxycamptothecin (317 mg, 0.87 mmol) in dimethylformamide (8 ml) and pyridine (1.5 ml) was added a solution of di-tert-butyl-dicarbonate (328 mg, 1.5 mmol) in dimethylformamide (2 ml). After stirring at room temperature for 3 hours, the mixture was partitioned between chloroform (100 ml) and water (100 ml). The chloroform phase was washed with 1 M hydrochloric acid (2×100 ml), dried over sodium sulfate, filtered, and concentrated under vacuum. The solid was recrystallized (chloroform-hexane) to give the 20(S)-10-tert-butoxycarbonyloxy-camptothecin (358 mg, 91% yield) as a yellow powder. $^1$H NMR (300 MHz. CDCl$_3$) δ 8.34 (s, 1 H), 8.23 (d, J=8 Hz, 1 H), 7.75 (d, J=2 Hz, 1 H), 7.67 (s, 1 H), 7.66 (dd, J=8, 2 Hz, 1 H), 5.75 (d.J=17 Hz, 1 H), 5.31 (d, J=17 Hz, 1 H), 5.27 (s, 2 H), 1.91 (sep., J=6 Hz, 2 H), 1.62 (s, 9 H), 1.06 (t, J=6Hz, 3 H).

A suspension of poly-(L-glutamic acid) (507 mg, 3.9 mmol free carboxylate) and 20(S)-10-tert-butoxycarbonyloxycamptothecin (103 mg, 0.23 mmol) in dimethylformamide (20 ml) was dissolved with gentle warming. When the resulting solution had cooled to room temperature, a solution of chloromethylpyridinium iodide (129 mg, 0.5 mmol) in dimethylformamide (2.5 ml) and a solution of 4-dimethylaminopyridine (131 mg, 1.1 mmol) in dimethylformamide (2.5 ml) were added sequentially. After stirring for 80 hours, the mixture was cooled in an ice bath and 10% aqueous sodium chloride solution (65 ml) was added over 30 minutes with vigorous stirring. After acidifying to pH 1–2 by slow addition of 0.5 M hydrochloric acid, the mixture was allowed to warm to room temperature and stirred for an additional 30 minutes. The solid was collected by centrifugation and the supernatant decanted. The solid was suspended in water (200 ml) and again isolated following centrifugation. This washing process was repeated 2 times and the solid was dried under vacuum. A suspension of the solid in 2% methanol-chloroform (25 ml) was treated with ultrasound for 90 minutes and filtered. This washing process was repeated and the solid was dried under vacuum to give PG-(10-tert-butoxycarbonyloxycamptothecin) (20-conjugated) (471 mg, 78% mass balance) as a yellow powder. The % loading was determined to be 10% based on the weight of 20(S)-10-tert-butoxycarbonyloxycamptothecin (53 mg) recovered from the methanol-chloroform washing solutions. $^1$H NMR (300 MHz. d$_6$-DMSO) δ 7.2–8.5 (multiple broad signals, Ar—H), 5.45, 5.20 (br.s, C-17, C-5 CH$_2$), 1.55 (s, 10-O-Boc), 0.85 (brs, C-18 CH$_3$).

PG-(10-tert-butoxycarbonyloxycamptothecin) (20-conjugated) (288 mg) was added in four portions to trifluoroacetic acid (50 ml) over a period 30 minutes. After stirring for 24 hours, the mixture was concentrated under vacuum to give PG-(10-OH-CPT) (251 mg, 87% mass balance). Integration of the $^1$H NMR spectrum indicates weight loading of 5%. $^1$H NMR (300 MHz, TFA-d) δ 9.15 (br. s., Ar—H); 7.2–8.5 (multiple broad signals, Ar—H); 5.6–6.0 (multiple signals, C-17, C-5 CH$_2$); 1.05 (br. triplet, C-18 CH$_3$).

Example 4

PG-gly-CPT

To a mixture of 20(S)-camptothecin (17.0 g, 48.8 mmol), N-(tert-butoxycarbonyl)-glycine (12.82 g, 73.2 mmol), and anhydrous dimethyformamide (170 ml); cooled in ice bath (4–6° C.) was added 4-dimethylaminopyridine (7.75 g, 63.5 mmol) portionwise over 15 minutes followed by 1-ethyl-3-(3-dimethylaminopropyl)carbodiimide (14.03 g, 73.2 mmol) portionwise over 20 minutes. After stirring at 5–10° C. (ice/water bath) for 3.5 hours, the mixture was cooled in an ice bath (4° C.) and water (275 ml) was added over 30 minutes with vigorous stirring. After stirring for an additional 15 minutes, the solid was filtered, washed with water (2×150 ml), ice-cold 0.1 M hydrochloric acid (300 ml), and water (3×100 ml). After lyophilization for 20 hours, the solid was recrystallized from ethyl acetate-methanol (1:4, 500 ml). After filtration, the solid was washed with ice-cold methanol (2×100 ml), and dried a to yield 20-O-(N-(tert-butoxycarbonyl)glycyl)camptothecin (22.5 g, 91% yield). Proton NMR was identical to that of an authentic sample.

To a suspension of 20-O-(N-(tert-butoxycarbonyl)glycyl) camptothecin (48.6 g, 93.6 mmol) in anhydrous ethyl acetate (125 ml), cooled in an ice bath, was added trifluoroacetic acid (250 ml) over 30 minutes. After 3.5 hours, the solvents were evaporated under reduced pressure. Recrystallization from hexanes-methanol-ethyl acetate (1:2:20, 575 ml) yielded a solid which was filtered, washed with ethyl acetate (150 ml), and dried under vacuum to provide 20-O-(glycyl) camptothecin trifluoroacetic acid salt (46.4 g, 93% yield) as a yellow powder. $^1$H NMR (TFA-d): δ 9.35 (s, 1H), 8.25–8.45 (m, 3H), 8.05 (t, J=7.3 Hz, 1H), 7.82 (s, 1H), 5.80 (d, J=18.1 Hz, 1H), 5.70 (s, 2H), 5.55 (d, J=18.1 Hz, 1H), 4.42 (d, J=17.6 Hz, 1H), 4.30 (d, J=17.6 Hz, 1H), 2.10–2.30 (m, 2H), 1.00 (t, J=7.4 Hz, 3H).

To a solution of poly-(L-glutamic acid) (1.24 g) in anhydrous dimethylformamide (31 ml) was added 20-O-(glycyl) camptothecin trifluoroacetic acid salt (1.0 g, 1.9 mmol). After cooling to 0° C., dimethylaminopyridine (707 mg, 5.79 mmol) was added in portions followed by a solution of 1,3-diisopropylcarbodiimide (292 mg, 2.32 mmol) in dimethylformamide (1 ml), which was added over 20 minutes. The mixture was allowed to warm to room temperature. After stirring for 2 days, the mixture was cooled in an ice bath and 10% aqueous sodium chloride solution (75 ml) was added over 30 minutes. The mixture was acidified to pH 2.5 by addition of 1 M hydrochloric acid. After stirring at room temperature for 1 hour, the solid was filtered, washed with water (4×100 ml), and dried under vacuum. The solid was suspended in 2% methanol-dichloromethane (75 ml), stirred for 1 hour, and filtered. This washing process was repeated 3 times with 2% methanol-dichloromethane, once with acetonitrile (100 ml) and once with water (100 ml). The solid was dried under vacuum for 2 days to yield PG-gly-CPT (1.88 g, 93% mass balance) as a yellow powder. $^1$H NMR (300 MHz in TFA-d) δ 9.45 (s, C-7H), 8.30–8.52 (m, aromatic protons), 8.27 (t, J=6.6 Hz, aromatic protons), 7.95 (s, aromatic proton), 5.92 (d, J=18.3 Hz, lactone proton), 5.72 (s, 5-H$_2$) 5.60 (d, J=18.3 Hz, lactone proton), 4.80 (br s), 4.30–4.70 (m, glycine methylene protons), 2.00–2.70 (m), 1.10 (br s).

Example 5

PG-gly-gly-CPT

After stirring a mixture of 20-O-(glycyl)camptothecin trifluoroacetic acid salt (2.60 g, 5.0 mmol) and N-(tert-butoxycarbonyl)glycine (2.63 g, 15.0 mmol) in anhydrous dimethylformamide (50 ml) for 30 minutes), it was cooled in ice bath and 4-dimethylaminopyridine (1.83 g, 15.0 mmol) was added. Diisopropylcarbodiimide (1.89 g, 15.0 mmol) was added over 30 minutes and the reaction mixture was allowed to warm to room temperature. After stirring for 16 hours, the mixture was treated with water (100 ml) and extracted with dichloromethane (3×100 ml). The combined organic extracts were washed with water (100 ml), 0.1 M hydrochloric acid (100 ml), water (100 ml), and dried over anhydrous sodium sulfate. After concentrating under reduced pressure, the residue was purified by flash chromatography on a silica gel eluting with 4% methanol-dichloromethane to provide 20-O-((N-(tert-butoxycarbonyl)glycyl)glycyl)camptothecin (1.30 g, 45% yield) as a yellow powder. $^1$H NMR (CDCl$_3$): δ 8.35 (s, 1H), 8.22 (d, J=8.38 Hz, 1H), 7.91 (d, J=8.07, 1H) 7.76–7.85 (m, 1H), 7.65 (t, J=7.4 Hz, 1H), 7.26 (s, 1H), 7.10 (s, 1H), 5.70 (d, J=17.25 Hz, 1H), 5.40 (d, J=17.25 Hz, 1H), 5.25 (s, 2H), 5.10 (brs, 1H), 3.70–4.45 (m, 4H), 2.05–2.30 m (m, 2H), 1.38 (s, 9H), 0.95 (t, J=7.47 Hz, 3H).

A solution of 20-O-((N-(tert-butoxycarbonyl)glycyl)glycyl)camptothecin (1.20 g, 2.10 mmol) in trifluoroacetic acid-dichloromethane (1:1, 4 ml) was stirred for 1 hour at room temperature. After evaporation of the solvents under reduced pressure, the residue was triturated with ethyl acetate (50 ml). The solid was filtered, washed with dichloromethane (40 ml), and dried under vacuum to yield 20-O-(glycyl-glycyl)camptothecin trifluoroacetic acid salt (1.0 g, 82% yield) as a yellow powder. $^1$H NMR (TFA-d): δ 9.45 (s, 1H), 8.10–8.50 (m, 3H), 7.95 (s, 1H), 5.90 (d, J=18.3 Hz, 1H), 5.80 (s), 5.65 (d, J=18.3 Hz, 1H), 4.10–4.60 (m, 4H), 2.20–2.50 (m, 2H), 1.10 (t, J=7.4 Hz, 3H).

To a mixture of 20-O-(glycyl-glycyl)camptothecin trifluoroacetic acid salt (220 mg, 0.38 mmol) and poly-L-glutamic acid (532 mg) in anhydrous dimethylformamide (14.5 ml), cooled in ice bath, was added N,N-dimethylaminopyridine (140 mg, 1.15 mmol). A solution of 1,3-diisopropylcarbodiimide (58 mg, 0.46 mmol) in dimethyformamide (0.5ml) was added over 20 minutes. And the mixture was allowed to warm to room temperature. After stirring under an argon atmosphere for 35 hours, the mixture was cooled in an ice bath and 10% aqueous sodium chloride solution (35 ml) was added over 30 minutes. After stirring for 1 hour, the mixture was acidified to pH 2.5 by addition of 1 M hydrochloric acid. The solid was filtered, washed with water (3×75 ml), dried under vacuum, washed with 2% methanol-dichloromethane (4×50 ml), dried under vacuum, washed with acetonitrile (100 ml), washed with water (100 ml), and dried under vacuum to provide PG-gly-gly-CPT (625 mg, 88% mass balance) as a yellow powder. $^1$H NMR (300 MHz in TFA-d): δ 9.45 (s, C-7H), 7.85–8.6 (aromatic protons), 5.92 (d, J=18.3 Hz, lactone proton), 5.70 (s) 5:62 (d, J=18.3 Hz, lactone proton), 4.20–5.10 (m), 32.10–2.90 (m), 1.00 (s).

Example 6

PG-gly-gly-gly-CPT

To a solution of ((N-(tert-butoxycarbonyl)glycyl)glycyl)glycine (1.99, 6.88 mmol) and 20(S)-camptothecin (1.20 g, 3.44 mmol) in anhydrous dimethylformamide (20 ml), cooled to 0° C., was added N,N-dimethylaminopyridine (630 mg, 5.16 mmol). 1,3-Diisopropylcarbodiimide (0.96 g, 7.6 mmol) was added slowly and the reaction mixture was allowed to warm to room temperature. After stirring for 16 hours, the mixture was cooled in an ice bath, treated with water (55 ml), and extracted with dichloromethane (3×50 ml). The combined organic extracts were washed sequentially with 0.1 M hydrochloric acid (2×50 ml) and water (2×50 ml) and dried over sodium sulfate. After evaporation of the solvent under reduced pressure, the residue was purified by flash chromatography on silica gel eluting with 4% methanol-dichloromethane to provide 20-O-(((N-(tert-butoxycarbonyl)glycyl)glycyl)glycyl)camptothecin (1.52 g, 71% yield) as a pale yellow powder. $^1$H NMR (CDCl$_3$): δ 8.40 (s, 1H), 8.25(d, J=8.38 Hz, 1H), 7.91(d, J=8.07, 1H), 7.76–7.85 (m, 1H), 7.65(t, J=7.4Hz, 1H), 7.26 (s, 1H), 7.05 (br s, 1H), 5.65 (d, J=17.25 Hz, 1H), 5.40 (d, J=17.25 Hz, 1H), 5.25 (s, 2H), 5.15 (br s, 1H), 3.70–4.45 (m, 6H), 2.15–2.35 (m, 2H), 1.45(s, 9H), 0.95(t, J=7.47 Hz, 3H).

A solution of 20-O-(((N-(tert-butoxycarbonyl)glycyl)glycyl)glycyl)camptothecin (1.50 g, 2.42 mmol) in trifluoroacetic acid-dichloromethane (1:1, 5 ml) was stirred for 1 hour at room temperature. After evaporation of the solvents under reduced pressure, the residue was triturated with ethyl acetate (30 ml). The solid was filtered, washed with dichloromethane (50 ml), and dried under vacuum to yield 20-O-(glycyl-glycyl-glycyl)camptothecin trifluoroacetic acid salt (1.3 g, 85% yield) as a yellow powder. $^1$H NMR (DMSO-d$_6$): δ 8.78 (s, 1H), 7.70–8.65 (m, 4H), 7.10 (s, 1H), 5.55 (s, 2H), 3.95–4.30 (m, 2H), 3.85 (s, 2H), 3.51 (s, 2H), 2.10–2.25 (m, 2H), 0.95 (t, J=7.4 Hz, 3H).

To a mixture of 20-O-(glycyl-glycyl-glycyl)camptothecin trifluoroacetic acid salt (940 mg, 1.49 mmol), and poly-(L-glutamic acid) (956 mg) in anhydrous dimethylformamide (29.5 ml), cooled in ice bath, was added N,N-dimethylaminopyridine (545 mg, 4.47 mmol). A solution of 1,3-diisopropylcarbodiimide (275 mg, 1.78 mmol) in dimethyformamide (0.5ml) was added over 20 minutes. After stirring under an argon atmosphere for 3 days, the mixture was cooled in ice bath and 10% aqueous sodium chloride solution (69 ml) was added over 30 minutes. After stirring for 1 hour, the mixture was acidified to pH 2.5 by addition of 1 M hydrochloric acid. The solid was filtered, washed with water (3×75 ml), dried under vacuum, washed with 2% methanol-dichloromethane (3×50 ml), dried under vacuum, washed with acetonitrile (100 ml), washed with water (100 ml), and dried under vacuum to yield PG-gly-gly-gly-CPT (1.50 g, 87% mass balance) as a yellow powder. $^1$H NMR,(300 MHz in TFA-d): δ 9.45 (s, C-7H), 7.85–8.50 (aromatic protons), 5.92 (d, J=18.3 Hz, lactone proton), 5.70 (s) 5.62 (d, J=18.3 Hz, lactone proton), 4.10–5.00 (m), 2.05–2.75 (m), 1.05 (s).

Example 7

PG-ala-CPT

To a solution of N-(tert-butoxycarbonyloxy)alanine (568 mg, 3.0 mmol) in anhydrous dimethylformamide (8 ml), cooled to 0° C., was added 20(S)-camptothecin (348 mg, 1.0 mmol) and dimethylaminopyridine (244 mg, 2.0 mmol). 1,3-Diisopropylcarbodiimide (379 mg, 3.0 mmol) was added slowly and the reaction mixture was allowed to warm to room temperature. After stirring for 16 hours, the mixture was treated with water (50 ml) and extracted with dichloromethane (4×40 ml). The combined organic extracts were washed sequentially with 0.1 M hydrochloric acid (2×50 ml), water (2×50 ml), 0.1 M aqueous sodium bicarbonate solution (2×25 ml), and water (2×50 ml). After drying over sodium sulfate, the solvent was evaporated under reduced pressure. The residue was purified by flash chromatography on silica gel eluting with 2% methanol-dichloromethane to provide 20-O-(N-(tert-butoxycarbonyloxy)alanyl) camptothecin (420 mg, 81% yield) as a yellow powder. $^1$H NMR(CDCl$_3$): δ 8.35 (s, 1H), 8.22 (d, J=8.38 Hz, 1H), 7.91(d, J=8.07, 1H), 7.76–7.85(m, 1H), 7.65 (t, J=7.4 Hz, 1H), 7.26 (s, 1H), 5.70 (d, J=17.25 Hz, 1H), 5.40 (d, J=17.25 Hz, 1H), 5.25 (s, 2H), 4.95 (br s, 1H), 4.45 (br t, 1H), 2.05–2.30 m (m, 2H), 1.55 (d, 3H), 1.45 (s, 9H), 0.95 (t, J=7.47 Hz, 3H).

A solution of 20-O-(N-(tert-butoxycarbonyloxy)alanyl) camptothecin (300 mg, 0.57 mmol) in trifluoroacetic acid-dichloromethane (1:1, 2 ml) was stirred for 1 hour at room temperature. After evaporation of the solvents under reduced pressure, the residue was triturated with 10% methanol-chloroform (12 ml). Filtration provided 20-O-(alanyl)camptothecin trifluoroacetic acid salt (318 mg, 87% yield) as a yellow powder which was used immediately to the next reaction.

To a stirred suspension of 20-O-(alanyl)camptothecin trifluoroacetic acid salt (114 mg, 0.21 mmol), poly-(L-glutamic acid) (280 mg) and N,N-dimethylaminopyridine (77 mg, 0.63 mmol) in anhydrous dimethylformamide (8.5 ml) was added a solution of 1,3-diisopropylcarbodiimide (34.5 mg, 0.273 mmol) in dimethylformamide (0.5 ml) over 20 minutes. The mixture was stirred under an argon atmosphere for 2 days. After cooling in ice bath, 10% aqueous sodium chloride solution (21 ml) was added over 30 minutes. After stirring for 1 hour, the mixture was adjusted to pH 2.5 by addition of 1 N hydrochloric acid. The solid was filtered, washed with water (5×25 ml), and dried under vacuum. The solid was washed with 2% methanol-dichloromethane (4×50 ml) and dried under vacuum to provide the PG-ala-CPT (330 mg, 81% mass balance) as a yellow powder. $^1$H NMR (300 MHz in TFA-d): δ 9.45 (s, C-7H), 7.85–8.6 (aromatic protons), 5.92 (d, J=18.3 Hz, lactone proton), 5.70 (s) 5.62 (d, J=18.3 Hz, lactone proton), 4.80–6.05 (m), 3.80–4.50 (m), 1.20–2.80 1.70 (br s), 1.00(s).

Example 8

PG-(β-ala)-CPT

To a solution of N-tert-butoxycarbonyl-β-alanine (568 mg, 3.0 mmol) in anhydrous dimethylformamide (8 ml), cooled to 0° C., was added 20(S)-camptothecin (348 mg, 1.0 mmol) and dimethylaminopyridine (244 mg, 2.0 mmol). 1,3-Diisopropylcarbodiimide (379 mg, 3.0 mmol) was added slowly and the reaction mixture was allowed to warm to room temperature. After stirring for 16 hours, the mixture was diluted with water (50 ml) and extracted with dichloromethane (4×40 ml). The combined organic extracts were washed sequentially with 0.1 M hydrochloric acid (2×50 ml), water (2×50 ml), 0.1 M aqueous sodium bicarbonate solution (2×25 ml), and water (2×50 ml). After drying over sodium sulfate, the solvent was evaporated under reduced pressure. The residue was purified by flash chromatography on silica gel eluting with 2% methanol-dichloromethane to provide 20-O-(N-tert-butoxycarbonyl-β-alanyl) camptothecin (431 mg, 83% yield) as a pale yellow powder. $^1$H NMR (CDCl$_3$): δ 8.35 (s, 1H), 8.22 (d, J=8.38 Hz, 1H), 7.91(d, J=8.07, 1H), 7.76–7.85(m, 1H), 7.65 (t, J=7.4 Hz, 1H), 7.26 (s, 1H), 5.70 (d, J=17.25 Hz, 1H), 5.40 (d, J=17.25 Hz, 1H), 5.25 (s, 2H), 5.15 (br s, 1H), 3.30–3.50 (m, 2H), 2.55–2.80m (m, 2H), 2.15–2.25(m, 2H), 1.45 (s, 9H), 0.95 (t, J=7.47 Hz, 3H).

A solution of 20-O-(N-tert-butoxycarbonyl-β-alanyl) camptothecin (250 mg, 0.48 mmol) in trifluoroacetic acid-dichloromethane (1:1, 2 ml) was stirred at room temperature for 1 hour. After evaporation of the solvent under reduced pressure, the residue was triturated with methanol-hexanes-dichloromethane (1:2:7). Filtration provided 20-O-(β-alanyl)camptothecin trifluoroacetic acid salt (241 mg, 94% yield) as a yellow powder. $^1$H NMR (DMSO-d$_6$): δ 8.78 (s, 1H), 8.05–8.50 (m, 2H), 7.60–7.94 (m, 2H), 7.15 (s, 1H), 5.55 (s, 2H), 5.30 (s, 2H), 2.80–3.60 (m, 4H), 2.15–2.25 (m, 2H), 1.00 (t, J=7.4 Hz, 3H).

To a stirred mixture of 20-O-(β-alanyl)camptothecin trifluoroacetic acid salt (241 mg, 0.45 mmol), poly-L-glutamic acid (326.mg), and N,N-dimethylaminopyridine (165 mg, 1.35 mmol) in anhydrous dimethylformamide (12.5 ml) was added a solution of 1,3-diisopropylcarbodiimide (74 mg, 0.59 mmol) in dimethyformamide (0.5ml) over 20 minutes. After stirring under an argon atmosphere for 2 days, the mixture was cooled in ice bath and 10% aqueous sodium chloride solution (30 ml) was added over 30 minutes. After stirring for 1 hour, the mixture was acidified to pH 2.5 by addition of 1 M hydrochloric acid. The solid was filtered, washed with water (5×25 ml), and dried under vacuum. The solid was washed with 2% methanol-dichloromethane (4×50 ml) and dried under vacuum to provide PG-(β-ala)-CPT (485 mg, 94% mass balance) as a yellow powder. $^1$H NMR (300 MHz in TFA-d): δ 9.45 (s, C-7H), 7.85–8.6 (aromatic protons), 5.92 (d, J=18.3 Hz, lactone proton), 5.70 (s) 5.62 (d, J=18.3 Hz, lactone proton), 4.70–5.10 (m), 3.65–3.90 (m), 2.00–3.10 (m), 1.00 (s).

Example 9

PG-(4-NH-butyryl)-CPT

To a solution of 4-(tert-butoxycarbonylamino)butyric acid (203 mg, 3.0 mmol) in anhydrous dimethylformamide (8 ml), cooled to 0° C., was added 20(S)-camptothecin (348 mg, 1.0 mmol), N,N-dimethylaminopyridine (244 mg, 2.0 mmol), followed by 1,3-diisopropylcarbodiimide (379 mg, 3.0 mmol), which was added slowly. The reaction mixture was allowed to warm to room temperature. After stirring for 16 hours, the mixture was treated with water (50 ml) and extracted with dichloromethane (4×40 ml). The combined organic extracts were washed with 0.1 M hydrochloric acid (2×50 ml), water (2×50 ml), 0.1 M aqueous sodium bicarbonate solution (2×25 ml), and water (2×50 ml). After drying over sodium sulfate, the solvent was evaporated under reduced pressure. The residue was purified by flash chromatography on a silica gel eluting with 2% methanol-dichloromethane to provide 20-O-(4-(tert-butoxycarbonylamino)butyryl)camptothecin (432 mg, 81% yield) as a yellow powder. $^1$H NMR (CDCl$_3$): δ 8.35 (s, 1H), 8.22 (d, J=8.38 Hz, 1H), 7.91(d, J=8.07, 1H), 7.76–7.85 (m, 1H), 7.65 (t, J=7.4 Hz, 1H), 7.26 (s, 1H), 5.70 (d, J=17.25 Hz, 1), 5.40 (d, J=17.25 Hz, 1H), 5.25 (s, 2H), 4.85 (brs, 1H), 3.05–3.30 (m, 2H), 2.40–2.60 (m, 2H), 2.05–2.30 m (m, 2H), 1.75–1.90 (m, 2H), 1.40 (s, 9H), 0.95 (t, J=7.47 Hz, 3H).

A solution of 20-O-(4-(tert-butoxycarbonylamino)butyryl)camptothecin (400 mg, 0.75 mmol) in trifluoroacetic acid-dichloromethane (1:1, 2 ml) was stirred for 1 hour at room temperature. After evaporation of solvents under reduced pressure, the residue was triturated with 10% methanol-dichloromethane (12 ml). Filtration yielded 20-O-(4-amninobutyryl)camptothecin trifluoroacetic acid salt (331 mg, 83% yield) as a yellow solid. $^1$H NMR (DMSO-d$_6$): δ 8.78 (s, 1H), 8.05–8.45 (m, 2H), 7.65–7.94 (m, 2H), 7.05 (s, 1H), 5.55 (s, 2H), 5.30 (s, 2H), 2.60–2.85 (m, 4H), 2.00–2.25 (m, 2H), 1.70–1.90 (m, 2H), 1.00 (t, J=7.4 Hz, 3H).

To a suspension of 20-O-(4-aminobutyryl)camptothecin trifluoroacetic acid salt (250 mg, 0.46 mmol), poly-(L-glutamic acid) (414 mg), and N,N-dimethylaminopyridine (168 mg, 1.38 mmol) in anhydrous dimethylformamide (13.5 ml) was added a solution of 1,3-diisopropylcarbodiimide (75 mg, 0.6 mmol) in dimethyformamide (0.5 ml) over 20 minutes. After stirring under argon atmosphere for 2 days, the mixture was cooled in an ice bath and 10% aqueous sodium chloride solution (35 ml) was added over 30 minutes. After stirring for an additional 1 hour, the mixture was acidified to pH 2.5 by addition of 1 M hydrochloric acid and filtered. The solid was washed with water (5×25 ml), dried under vacuum, washed with 2% methanol-dichloromethane (4×50 ml), and dried under vacuum to yield PG-(4-NH-butyryl)-CPT (574 mg, 94% mass balance) as a yellow powder. $^1$H NMR (300 MHz in TFA-d) δ 9.45 (s, C-7H), 8.30–8.52 (m, aromatic protons), 8.27 (t, J=6.6 Hz, aromatic protons), 7.95 (s, aromatic proton), 7.20 (s, aromatic proton), 5.92 (d, J=18.3 Hz, lactone proton), 5.70 (s), 5.62 (d, J=18.3 Hz, lactone proton), 4.70–5.05 (mn), 3.45–3.70 (m), 2.02–3.00 (m), 1.05 (br s).

Example 10

PG-(2-O-acetyl)-CPT

20-O-(2-Hydroxyacetyl)camptothecin was prepared according to the procedure described in Greenwald et al. *Bioorg. Med. Chem.* 6:551–562 (1998).

Chloromethylpyridinium iodide (163 mg, 0.64 mmol) and 4-dimethylaminopyridine (89 mg, 0.73 mmol) were added sequentially to a solution of 20-O-(2-hydroxyacetyl)camptothecin (80 mg, 0.20 mmol) and poly-(L-glutamic acid) (411 mg) in dimethylformamide (20 ml). After stirring for 18 hours, the mixture was cooled in an ice bath and 10% aqueous sodium chloride solution (50 ml) was added over a period of 1 hour. The pH of the resulting mixture lowered to 2 by slow addition of 0.1 M hydrochloric acid. The precipitate was collected after centrifugation and suspended in water (25 ml) and again collected after centrifugation. This sequence was repeated two more times and the solid was dried under vacuum. The solid was suspended in chloroform-methanol (95:5, 10 ml) and treated with ultrasound for 90 minutes. The mixture was filtered and the solid was dried under vacuum to provide PG-(2-O-acetyl)-CPT (404 mg, 86% mass balance) as a pale yellow solid. A weight loading of 15% was estimated based on the weight of recovered 20-O-(2-hydroxyacetyl)camptothecin. $^1$H NMR (300 MHz, d$_6$-DMSO) δ 7.6–8.7 (multiple broad signals CPT Ar—H), 7.15 (s, CPT Ar—H), 4.8–5.6 (broad signals, CPT lactone, C5 —CH$_2$—), 3.7–4.3 (broad signal, PG α-CH), 3.1–3.4 (broad singlet, PG), 1.7–2.4 (broad sigals, PG), 1.0 (br signal, CPT —CH$_2$CH$_3$).

Example 11

PG-(4-O-butyryl)-CPT

To a mixture of 20(S)-camptothecin (300 mg, 0.86 mmol) and 4-benzyloxybutyric acid (501 mg, 2.58 mmol) in anhydrous dimethylformamide (12 ml) cooled to 0° C. was added N,N-dimethylaminopyridine (210 mg, 1.72 mmol). 1,3-Diisopropylcarbodiimide (326 mg, 2.58 mmol) was added slowly and the reaction mixture was allowed to warm to room temperature. After stirring for 15 hours, the mixture was treated with water (50 ml) and extracted with dichloromethane (4×40 ml). The combined organic extracts were washed with 0.1 M hydrochloric acid (2×50 ml), with water (2×50 ml) and dried over sodium sulfate. After evaporating the solvent under reduced pressure, the residue was purified by flash chromatography on silica gel eluting with 2% methanol-dichloromethane to provide 20-O-(4-benzyloxybutyryl)camptothecin (432 mg, 81% yield) as a yellow powder. $^1$H NMR (CDCl$_3$): δ 8.35 (s, 1H), 8.22 (d, J=8.38 Hz 1H), 7.91(d, J=8.07, 1H), 7.76–7.85 (m, 1H), 7.65 (t, J=7.4 Hz, 1H), 7.20–7.40 (m, 6H), 5.70 (d, J=17.25 Hz, 1H), 5.40 (d, J=17.25 Hz, 1H), 5.25 (s, 2H), 4.52 (brs, 2H), 3.45–3.60 (m, 2H), 2.60–2.75 (m, 2H), 1.90–2.35 (m, 4H), 0.95 (t, J=7.47 Hz, 3H).

To a mixture of 20-O-(4-benzyloxybutyryl)camptothecin (1.0 g, 1.90 mmol) and 10% palladium on carbon (50% water, 200 mg) suspended in ethanol-1,4-dioxane (4:1, 20 ml) was added cyclohexene (0.78 g, 9.5 mmol). After heating at gentle reflux for 15 hours, the mixture was cooled and the catalyst was removed by filtration. After concentrating under reduced pressure, the solid residue was crystallized with methanol (8.0 ml) to provide 20-O-(4-hydroxybutyryl)camptothecin (679 mg, 82% yield) as a pale yellow powder. $^1$H NMR (CD$_3$OD): δ 8.40 (s, 1H), 8.05 (d, J=8.38 Hz 1H), 7.91(d, J=8.07, 1H), 7.76–7.85 (m, 1H), 7.65 (t, J=7.4 Hz, 1H), 7.30 (s, 1H), 5.70 (d, J=17.25 Hz, 1H), 5.40 (d, J=17.25 Hz, 1H), 5.25 (s, 2H), 3.50 (t, 3H), 2.50 (t, 2H), 1.70–2.30 (m, 4H), 0.95 (t, J=7.47 Hz, 3H).

To a mixture of 20-O-(4-hydroxybutyryl)camptothecin (114 mg, 0.26 mmol) and poly-(L-glutamic acid) (265 mg, 1.8 mmol) in anhydrous dimethylformamide (7.5 ml) was added dimethylaminopyridine (6 mg, 0.052 mmol). 1,3-Diisopropylcarbodimide (43 mg, 0.34 mmol) was added slowly and the reaction mixture was stirred under argon for 5 hours. After cooling in ice bath, 10% aqueous sodium chloride solution (18 ml) was added dropwise. The pH was adjusted to 2.5 by addition of 1 N hydrochoric acid. After stirring at room temperature for 1 hour, the mixture was filtered. The solid was washed with water (3×30 ml) and dried under vacuum. The powder was washed with 2% methanol-dichloromethane (4×30 ml) and dried under vacuum to yield PG-(4-O-butyryl)-CPT (360 mg, 95% mass balance) as a yellow powder. $^1$H NMR (300 MHz in TFA-d): δ 9.45 (s, C-7H), 8.30–8.52 (m, aromatic protons), 8.27 (t, J=6.6 Hz, aromatic proton), 7.95 (s, aromatic proton), 5.92 (d, J=18.3 Hz, lactone proton), 5.70 (s,) 5.62 (d, J=18.3 Hz, lactone proton), 4.90 (br s), 4.40 (s), 2.00–2.90 (m), 1.10 (br s).

Example 12

PG-(γ-glu)-CPT

To a solution of N-(tert-butoxycarbonyl)glutamyl-γ-tert-butyl ester (910 mg, 3.0 mmol) in anhydrous dimethylformamide (8 ml), cooled to 0° C., was added 20(S)-camptothecin (348 mg, 1.0 mmol) and N,N-dimethylaminopyridine (244 mg, 2.0 mmol). 1,3-Diisopropylcarbodiimide (379 mg, 3.0 mmol) was added slowly and the reaction mixture was allowed to warm to room temperature. After stirring for 16 hours, the mixture was treated with water (50 ml) and extracted with dichloromethane (4×40 ml). The combined organic extracts were washed sequentially with 0.1 M hydrochloric acid (2×50 ml), water (2×50 ml), 0.1 M aqueous sodium bicarbonate solution (2×25 ml), and water (2×50 ml). After drying over sodium sulfate, the solvent was evaporated under reduced pressure. The residue was purified by flash chromatography on silica gel eluting with 2% methanol-dichloromethane to provide 20-O-(N-(tert-butoxycarbonyl)-γ-glutamyl)camptothecin α-tert-butyl ester (432 mg, 81% yield) as a yellow powder. $^1$H NMR (CDCl$_3$): δ 8.40 (s, 1H), 8.22 (d, J=8.38 Hz, 1H), 7.91 (d, J=8.07, 1H), 7.65–7.85 (m, 2H), 7.26 (s, 1H), 5.70 (d, J=17.25 Hz, 1H), 5.40 (d, j=17.25 Hz, 1H), 5.25 (s, 2H), 5.05 (br d, 1H), 4.10 (brs, 1H), 1.85–2.70 (m, 6H), 1.45 (s, 18H), 0.95 (t, J=7.47 Hz, 3H).

A solution of 20-O-(N-(tert-butoxycarbonyl)glutamyl) camptothecin α-tert-butyl ester (300 mg, 0.47 mmol) in dichloromethane-trifluoroacetic acid (1:1, 1 ml) was stirred at room temperature for 20 minutes. After evaporating the solvents under reduced pressure, the residue was triturated with methanol-dichloromethane-hexanes (1:2:2, 10 ml). Filtration provided 20-O-(γ-glutamyl)camptothecin (α-tert-butyl ester trifluoroacetic acid salt (239 mg, 79% yield) as a yellow solid. $^1$H NMR (DMSO-d$_6$): δ 8.78 (s, 1H), 7.70–8.20 (m, 3H), 7.05 (s, 1H), 5.55 (s, 2H), 5.30 (s, 2H), (brs, 1H), 1.90–2.85 (m, 6H) 1.50 (s, 9H), 1.00 (t, J=7.4 Hz, 3H).

To a mixture of 20-O-(γ-glutamyl)camptothecin α-tert-butyl ester trifluoroacetic acid salt (239 mg, 0.37 mmol), poly-(L-glutamic acid) (395 mg, 2.69 mmol) and N,N-dimethylaminopyridine (135.6 mg, 1.11 mmol) in anhydrous dimethylformamide (12.5 ml) was added a solution of 1,3-diisopropylcarbodiimide (61 mg, 0.48 mmol) in dimethyformamide (0.5 ml) over 20 minutes. After stirring under argon atmosphere for 2 days, the mixture was cooled in ice bath and 10% aqueous sodium chloride solution (30 ml) was added over 30 minutes. After stirring for 1 hour, the mixture was acidified to pH 2.5 by addition of 1 M hydrochloric acid. The solid was filtered, washed with water (4×30 ml) and dried under vacuum. The solid was washed with 2% methanol-dichloromethane (4×50 ml) and dried under vacuum to provide PG-(γ-glu)-CPT α-tert-butyl ester (556 mg, 94% mass balance) as a yellow powder. $^1$H NMR (300 MHZ in TFA-d): δ 9.45 (s, C-7H), 7.90–8.60 (m, aromatic protons), 7.25 (s, aromatic proton), 5.92 (d, J=18.3 Hz, lactone proton), 5.70 (s), 5.62 (d, J=18.3 Hz, lactone proton), 4.60–5.0 (m), 2.05–3.00 (m), 1.55 (s), 1.10 (br s).

A solution of PG-(γ-glu)-CPT α-tert-butyl ester (550 mg) in trifluoroacetic acid (5 ml) was stirred at room temperature for 16 hours. After concentrating under reduced pressure, the residue was washed with water (100 ml) and dried under vacuum to yield PG-(γ-glu)-CPT (460 mg) as a yellow powder. $^1$H NMR (300 MHz in TFA-d): δ 9.45 (s, C-7H), 7.90–8.60 (m, aromatic protons), 5.92 (d, J=18.3 Hz, lactone proton), 5.70 (s), 5.62 (d, J=18.3 Hz, lactone proton), 4.60–5.0 (m), 2.05–3.00 (m), 1.05 (br s).

Example 13

PG-(10-O-CPT)

A suspension of poly-(L-glutamic acid) sodium salt (50 kD, 740 mg) in dimethylformamide (30 ml) was cooled in an ice bath. Methanesulfonic acid (0.3 ml, 4.6 mmol) was added and the mixture was stirred for 30 min. 10-Hydroxycamptothecin (166 mg, 0.45 mmol), chloromethylpyridinium iodide (190 mg, 0.74 mmol) and 4-dimethylaminopyridine (168 mg, 1.4 mmol were added sequentially. The mixture was allowed to warm to room temperature and stirred for vigorously for 20 hours. The mixture was cooled in an ice bath and 10% aqueous sodium chloride solution (100 ml) was added over 45 minutes with vigorous stirring. After acidifying to pH 1–2 by slow addition of 0.5 M hydrochloric acid, the mixture was allowed to warm to room temperature and stirred for an additional 30 minutes. The solid was collected by centrifugation and the supernatant decanted. The solid was suspended in water (200 ml) and again isolated following centrifugation. This washing process was repeated 2 times and the solid was dried under vacuum. A suspension of the solid in 2% methanol-chloroform (25 ml) was treated with ultrasound for 90 minutes and filtered. This washing process was repeated and the solid was dried under vacuum to give PG-(10-O-CPT) (674 mg, 93% mass balance) as a yellow powder. $^1$H NMR (300 MHz. $d_6$-DMSO) δ 7.2–8.6 (multiple broad signals, Ar-H), 5.45, 5.20 (br s, C-17, C-5 $CH_2$), 0.85 (br triplet, C-18 $CH_3$). The % loading was determined to be 13% based on the weight of 20(S)-10-hydroxycamptothecin recovered from the methanol-chloroform washing solutions.

Alternatively, PG-(10-O-CPT) was synthesized according to the method described above but using poly-(L-glutamic acid) in place of poly-(L-glutamic acid) sodium salt and methanesulfonic acid.

Example 14

PG-gly-(10-O-CPT)

A solution of N-tert-butoxycarbonylglycine (603 mg, 3.4 mmol) in dimethylformamide (10 ml) was treated with diisopropylcarbodiimide (0.27 ml, 1.7 mmol). After stirring for 15 min this solution was added to a solution of 20(S)-10-hydroxycamptothecin (406 mg, 1.11 mmol) and pyridine (0.9 ml) in dimethylformamide (10 ml). After stirring for 4 hours, the mixture was poured into water (300 ml) and extracted with chloroform (4×75 ml). The combined chloroform extracts were washed with 0.1 M hydrochloric acid (2×100 ml) followed by saturated aqueous sodium bicarbonate solution (2×100 ml), dried over sodium sulfate, filtered, and concentrated under vacuum. The residue was purified by flash chromatography on silica gel eluting with 2% methanol-chloroform to give 20(S)-10-(N-tert-butoxycarbonylglycyloxy)camptothecin (247 mg, 43%) as a pale yellow powder. $^1$H NMR (300 MHz. $CDCl_3$) δ 8.32 (s, 1H), 8.21 (d, J=8 Hz, 1 H), 7.70 (d, J=3 Hz, 1 H), 7.64 (s, 1 H), 7.56 (dd, J=8, 3 Hz, 1 H), 5.73 (d, J=15 Hz, 1 H), 5.28 (d, J=15 Hz, 1 H), 5.25 (s, 2 H), 5.17 (m, 1 H), 4.26 (d, J=7 Hz, 2 H), 1.88 (sep., J=6 Hz, 2H), 1.49 (s, 9 H), 1.04 (t, J=6 Hz, 3 H).

A solution of 20(S)-10-(N-tert-butoxycarbonylglycyloxy) camptothecin (206 mg, 0.39 mmol) in dichloromethane (10 ml) and trifluoroacetic acid (5 ml) was stirred for 90 minutes. After concentrating under vacuum, the residue was dissolved in chloroform (50 ml) and concentrated under vacuum. The residue was dissolved in toluene (50 ml) and concentrated under vacuum to provide 20(S)-10-(glycyloxy) camptothecin.

A solution of 20(S)-10-(glycyloxy)camptothecin in dimethylformamide (10 ml) was added to a solution of poly-(L-glutamic acid) (50 kD, 641 mg) in dimethylformamide (20 ml) followed by 4-dimethylaminopyridine (151 mg, 1.2 mmol) and diisopropylcarbodiimide (0.08 ml, 0.5 mmol). After stirring vigorously for 60 hours, the mixture was cooled in an ice bath and 10% aqueous sodium chloride solution (75 ml) was added over 1 hour with vigorous stirring. After acidifying to pH 1–2 by slow addition of 0.5 M hydrochloric acid, the mixture was allowed to warm to room temperature and stirred for 30 minutes. The solid was collected by centrifugation and the supernatant decanted. The solid was suspended in water (200 ml) and again isolated following centrifugation. This washing process was repeated 2 times and the solid was dried under vacuum. A suspension of the solid in 2% methanol-chloroform (25 ml) was treated with ultrasound for 90 minutes and filtered. This washing process with 2% methanol-chloroform was repeated. The solid was dried under vacuum to give PG-gly-(10-O-CPT) (560 mg, 70%) as a yellow powder. $^1$H NMR (300 MHz. $d_6$-DMSO) δ 7.2–8.8 (multiple broad signals, Ar—H), 5.45, 5.20 (br s, C-17, C-5 $CH_2$), 0.9 (br s, C-18 $CH_3$).

Example 15

PG-(9-NH-CPT)

To a mixture of 20(S)-9-aminocamptothecin (157 mg, 0.43 mmol) and poly-(L-glutamic acid) (38 kD, 628 mg), dried under vacuum for 4 hours, was added anhydrous dimethylformamide (35 ml). After cooling in an ice bath, 2-chloromethylpyridinium iodide (199 mg, 0.78 mmol) and N,N-dimethylaminopyridine (200 mg, 1.64 mmol) were added and the mixture was allowed to warm to room temperature. After stirring for 2 days, the mixture was cooled to 0° C. and 10% aqueous sodium chloride solution (82 ml) was added over 25 minutes. The mixture was acidified to pH 2.5 by addition of 1 M hydrochloric acid (3.5 ml) and stirred at room temperature for 1 hour. The precipitate was filtered, washed with water (4×50 ml), and dried under vacuum. The solid was ground to a powder and suspended in 2% methanol-dichloromethane (10 ml). After stirring for 3 hours, the solid was separated by centrifugation and the supernatant ddecanted. This washing process was repeated 4 times to effect complete removal of unreacted 20(S)-9-aminocamptothecin. The solid was dried under vacuum to yield PG-(9-NH-CPT) (592 mg, 80% mass balance based on the weight of recovered 20(S)-9-aminocamptothecin (45 mg)). $^1$H NMR (300 MHz in DMSO-$d_6$): δ 12.10 (s, —COOH), 8.80 (s), 6.50–8.5 (m), 5.15–5.8 (m), 3.10–4.35 (m), 1.42–2.62 (m,), 0.90 (br s, 19-$CH_3$).

The % weight loading of 20(S)-9-aminocamptothecin in this sample of PG-(9-NH-CPT) was determined to be 14% based on the weight of consumed 20(S)-9-aminocamptothecin (115 mg) during the coupling reaction.

Example 16

PG-gly-(9-NH-CPT)

20(S)-9-(N-tert-Butoxycabonylglycylamino)camptothecin was prepared by modification of the method described by Wall et al, J. Med. Chem. 1993, 36, 2689–2700. To a solution of N-tert-butoxycarbonylglycine (526 mg, 3.0 mmol) in anhydrous dimethylformamide (10 ml) was added 20(S)-9-aminocamptothecin (363 mg, 1.0 mmol) followed by 1,3-diisopropylcarbodiimide (379 mg, 3.0 mmol) over 30 minutes. After stirring under an argon atmosphere for 12 hours, the mixture was treated with water (50 ml) and extracted with dichloromethane.(3×100 ml). The combined organic extracts were washed with water (50 ml), 0.1 M hydrochloric acid (2×50 ml), 0.1 M saturated aqueous sodium bicarbonate solution, and water (50 ml). The solution was dried over sodium sulfate and concentrated under reduced pressure. The residue was crystallized (methanol-chloroform (1:9)) to provide 20(S)-9-(N-tert-butoxycabonylglycylamino)camptothecin (354 mg, 68% yield) as a yellow powder. $^1$H NMR (DMSO-$d_6$): δ 10.10 (s, 1H), 8.79 (s, 1H), 8.03, (d, J=7 Hz, 1H), 7.85 (t, J=7 Hz, 1H), 7.79 (d, J=7 Hz, 1H), 7.37 (s, 1H), (t, J=6 Hz, 1H), 6.53 (s, 1H), 5.44 (s, 2H), 5.29 (s, 2H), 3.92 (m, 2H), 1.88 (m, 2H), 1.44 (s, 9H), 0.89 (t, J=7Hz, 3H).

A solution of 20(S)-9-(N-tert-butoxycabonylglycylamino)camptothecin (80mg, 0.15 mmol) in trifluoroacetic acid-dichloromethane (1:1, 4 ml) was stirred for 1 hour at room temperature. Solvents were evaporated under reduced pressure and the solid was recrystallized (dichloromethane-diethyl ether (3:7, 50 ml) to yield 20(S)-9-(glycylamino) camptothecin trifluoroacetic acid salt (78 mg, 82% yield) as a brownish yellow powder.

To a stirred suspension of 20(S)-9-(glycylamino)camptothecin trifluoroacetic acid salt (78 mg, 0.15 mmol), poly-(L-glutamic acid) (38 kD, 222 mg), and N,N-dimethylaminopyridine (46 mg, 0.37 mmol) in anhydrous dimethylformamide (5.5 ml) was added a solution of 1,3-diisopropylcarbodiimide (17 mg, 0.14 mmol) in dimethylformamide (0.5 ml) over 20 minutes. After stirring under an argon atmosphere for 2 days, the mixture was cooled in an ice bath and 10% aqueous sodium chloride solution (15 ml) was added over 30 minutes. After stirring for an additional 1 hour, the mixture was acidified to pH 2.5 by addition of 1 M hydrochloric acid (1.5 ml) and filtered. The solid was washed with water (5×25 ml), dried under vacuum, washed with 2% methanol-dichloromethane (3×50ml), and dried under vacuum to yield PG-gly-(9-NH-CPT) (255 mg, 92% mass balance) as a brownish yellow powder. The % weight loading of 20(S)-9-aminocamptothecin in this sample of PG-gly-(9-NH-CPT) was determined to be 20% based on the weight of consumed 20(S)-9-aminocamptothecin in the coupling reaction.

Example 17

PG-gly-(10-OH-CPT)

Diisopropylcarbodiimide (0.36 ml, 2.3 mmol) was added to a solution of 20(S)-10-tert-butoxycarbonyloxycamptothecin (350 mg, 0.77 mmol), N-tert-butoxycarbonylglycine (403 mg, 2.3 mmol) and 4-dimethylaminopyridine (283 mg, 2.3 mmol) in dichloromethane (20 ml). After stirring for 20 hours, the mixture was diluted with chloroform (150 ml) and washed with 1 M hydrochloric acid (2×100 ml) followed by saturated aqueous sodium bicarbonate solution-water (1:1, 2×50 ml). The organic phase was dried over sodium sulfate, filtered, and concentrated under vacuum. The residue was purified by flash chromatography on silica gel eluting with 1% methanol-chloroform to give 20-O-(N-tert-butoxycarbonylglycyl)-10-(tert-butoxycarbonyloxy) camptothecin (250 mg, 52% yield) as a yellow powder. $^1$H NMR (300 MHz. CDCl$_3$) δ 8.34 (s, 1 H), 8.23 (d, J=8 Hz, 1 H), 7.74 (d, J=2 Hz, 1 H), 7.67(dd, J=8, 2 Hz, 1 H), 5.70(d, J=17 Hz, 1 H), 5.41 (d, J=17 Hz, 1 H), 5.27 (s, 2 H), 4.96 (m, 1 H), 4.29–4.03 (m, 2 H), 2.23 (d. sex., J=31, 6 Hz, 2 H), 1.63 (s, 9H), 1.43 (s, 9 H), 1.00 (t, J=6 Hz, 3 H).

A solution of 20-O-(N-tert-butoxycarbonylglycyl)-10-(tert-butoxycarbonyloxy)-camptothecin (250 mg, 0.4 mmol) in dichloromethane (40 ml) and trifluoroacetic acid (10 ml) was stirred for 60 minutes. After concentrating under vacuum, the residue was dissolved in methanol (10 ml). Toluene (50 ml) was added and the solution was concentrated under vacuum. This procedure was repeated 2 times to provide 20-O-glycyl-10-hydroxycamptothecin.

The 20-O-glycyl-10-hydroxycamptothecin, synthesized in the previous step, was dissolved in dimethylformamide (5 ml) and treated with N,N-diisopropylethylamine (0.2 ml, 1.1 mmol). This solution was added to a solution of poly-(L-glutamic acid) (37.7 kD, 640 mg) and diisopropylcarbodiimide (0.1 ml, 0.64 mmol) in dimethylformamide (25 ml). After stirring for 18 hours, the mixture was cooled in an ice bath and 10% aqueous sodium chloride solution (75 ml) was added over with vigorous stirring. After acidifying to pH 1–2 by slow addition of 0.5 M hydrochloric acid, the mixture was allowed to warm to room temperature and stirred for 1 hour. The solid was collected by centrifugation and the supernatant decanted. The solid was suspended in water (200 ml) and again isolated following centrifugation. This washing process was repeated 2 times and the solid was dried under vacuum. A suspension of the solid in 2% methanol-chloroform (25 ml) was treated with ultrasound for 90 minutes and filtered. This washing process was repeated. The solid was then dried under vacuum to give PG-gly-(10-OH-CPT) (663 mg, 83% mass balance) as a yellow powder: $^1$H NMR (300 MHz. $d_6$-DMSO) δ 7.1–8.5 (multiple broad signals, Ar—H), 5.45, 5.20 (br s, C-17, C-5 CH$_2$), 0.9 (br s, C-18 CH$_3$).

Example 18

PG-gly-(7-Et-10-OH-CPT)

20(S)-7-Ethyl-10-hydroxycamptothecin (SN 38) (333 mg, 0.85 mmol) was dissolved in a mixture of dimethylformamide (6 ml) and pyridine (2 ml). A solution of di-tert-butyl-dicarbonate (294 mg, 1.35 mmol) in dimethylformamide (2 ml) was added and the mixture was stirred at room temperature for 19 hours. The mixture was concentrated under vacuum and the residue was purified by flash chromatography on silica gel eluting with chloroform-methanol (99:1) to give 20(S)-10-tert-butoxycarbonyloxy-7-ethyl-camptothecin (337 mg, 80% yield) as a yellow powder. $^1$H NMR (300 MHz. CDCl$_3$) δ 8.24 (d, J=12 Hz, 1 H), 7.88 (d, J=4 Hz, 1 H), 7.63–7.70 (m, 2 H), 5.75 (d, J=16 Hz, 1 H), 5.31 (d, J=16 Hz, 1 H), 5.27 (s, 2 H), 3.28 (q, J=7 Hz, 2 H), 1.90 (sep., J=8 Hz, 2 H), 1.61 (s, 9 H), 1.43 (t, J=7 Hz, 3 H), 1.08 (t, J=8 Hz, 3 H).

1-(3-Dimethylaminopropyl)-3-ethylcarbodiimide hydrochloride (192 mg, 1.0 mmol) was added to a solution of 10-tert-butoxycarbonyloxy-7-ethylcamptothecin (150 mg, 0.30 mmol), N-(tert-butoxycarbonyl)glycine (178 mg, 1.0 mmol) and 4-dimethylaminopyridine (137 mg, 1.1 mmol) in dichloromethane (15 ml). After stirring for 24 hours, the mixture was diluted with chloroform (75 ml) and washed with 1 M hydrochloric acid (2×50 ml) and a solution of saturated aqueous sodium bicarbonate and Water (1:1, 2×50 ml). The organic phase was dried over sodium sulfate, filtered and concentrated under vacuum. The residue was purified by flash chromatography on silica gel eluting with chloroform-methanol (99:1) to give 20-O-(N-(tert-butoxycarbonyl)glycyl)-10-tert-butoxycarbonyloxy-7-ethylcamptothecin-(41 mg, 20% yield) as a yellow powder. $^1$H NMR (300 MHz. CDCl$_3$) δ 8.27 (d, J=9 Hz, 1 H), 7.90(d, J=3 Hz, 1 H), 7.68(dd, J=9,3 Hz, 1 H), 5.72(d, J=17 Hz, 1 H), 5.42 (d, J=17 Hz, 1 H), 5.25 (s, 2 H), 4.96 (m, 1 H), 4.29–4.03

(m, 2 H), 3.17 (q, J=7 Hz, 2 H), 2.23 (d. sex., J=31, 6 Hz, 2 H), 1.63 (s, 9 H), 1.48–1.38 (m, 12 H), 1.00 (t, J=6 Hz, 3 H).

20-O-(N-(tert-butoxycarbonyl)glycyl)-10-tert-butoxycarbonyloxy-7-ethylcamptothecin (40 mg, 0.06 mmol) was dissolved in dichloromethane (25 ml) and trifluoroacetic acid (15 ml) was added. After stirring for 1 hour, the mixture was concentrated under vacuum. The residue was dissolved in methanol (20 ml) and toluene (20 ml) was added. The solution was concentrated under vacuum. This procedure was repeated two additional times. The resulting solid was dissolved in dimethylformamide (3 ml) and treated with N,N-diisopropylethylamine (0.03 ml, 0.17 mmol). This solution was added to a solution of poly-(L-glutamic acid) (168 mg) and diisopropylcarbodiimide (0.02 ml, 0.13 mmol) in dimethylformamide (6 ml). After stirring for 21 hours, the mixture was cooled in an ice bath and 10% aqueous sodium chloride solution (30 ml) was added with vigorous stirring over 60 minutes. The pH of the mixture was then lowered to 1–2 by the slow addition of 0.5 M hydrochloric acid. The mixture was allowed to warm to room temperature and was stirred for an additional 60 min. The mixture was centrifuged and the supernatant was decanted. The solid was suspended in water (75 ml) and again separated by centrifugation. This sequence was repeated two more times and the solid was dried under vacuum for 24 hour. The solid was suspended in chloroform-methanol (92:2, 25 ml) and the resulting slurry was treated with ultrasound for 90 minutes. The mixture was filtered and the sequence was repeated. The solid was dried under vacuum to give PG-gly-(7-Et-10-OH-CPT) (112 mg, 54% mass balance) as a yellow powder. Integration of the $^1$H NM spectrum indicates weight loading of 12%. $^1$H NMR (300 MHz. d-TFA) δ 8.5-7.7 (multiple broad signals, Ar—H), 6.0–5.6 (br.signals, C-17, C-5 CH$_2$), 4.6 (m, gly CH$_2$), 3.5 (m, 7-Ethyl CH$_2$), 1.6 (br. t, 7-Ethyl CH$_3$), 0.9 (br t, C-18 CH$_3$).

Example 19

PG-gly-(7-t-BuMe$_2$Si-10-OAc-CPT)

To a solution of 20(S)-7-(tert-butyldimethylsilyl)-10-hydroxycamptothecin (DB 67; Bom et al. *J Med. Chem.* 43: 3970–80 (2000)) (38 mg, 0.08 mmol) in a mixture of dichloromethane (0.5 ml) and pyridine (0.1 ml, 1.2 mmol) was added acetic anhydride (0.04 ml, 0.42 mmol). After stirring for 20 hours, the reaction mixture was concentrated under vacuum. The residue was purified by flash chromatography on silica gel eluting with chloroform-methanol (99:1) to provide 10-acetoxy-7-(tert-butyldimethylsilyl)camptothecin (29 mg, 70%) as a yellow powder. $^1$H NMR (300 MHz, CDCl$_3$) δ 8.23 (d, 1 H, J=10 hz), 8.08 (d, 1 H, J=2 Hz), 7.67 (s, 1 H), 7.53 (dd, 1 H, J=10, 2 Hz), 5.75 (d, 1 H, J=15 Hz), 5.34 (s, 2 H), 5.30 (d, 1 H, J=15 Hz), 2.39 (s, 3 H), 1.88 (hep, 2 H, J=9Hz), 1.06 (t, 3 H, J=9 H), 0.98 (s, 9 H), 0.69 (s, 6 H).

1-(3-(Dimethylamino)propyl)-3-ethylcarbodiimide hydrochloride (35 mg, 0.18 mmol) was added to a solution of 10-acetoxy-7-(tert-butyldimethylsilyl)camptothecin (30 mg, 0.058 mmol), N-(tert-butoxycarbonyl)glycine (33 mg, 0.19 mmol), and 4-dimethylaminopyridine (16 mg, 0.13 mmol) in dichloromethane. After stirring for 20 hours, the mixture was diluted with dichloromethane (25 ml) and the resulting solution was washed with 1 M hydrochloric acid (2×20 ml). The organic phase was dried over sodium sulfate, filtered and concentrated under vacuum. The residue was purified by flash chromatography on silica gel eluting with 1% methanol-chloroform to provide 10-acetoxy-20-O-(N-(tert-butoxycarbonyl)glycyl)-7-(tert-butyldimethylsilyl) camptothec (24 mg, 61% yield) as a yellow powder. $^1$H NMR (300 MHz, CDCl$_3$) δ 8.23 (d, 1 H, J=10 hz), 8.11 (d, 1 H, J=2 Hz), 7.56 (dd, 1 H, J=10, 2 Hz), 7.22 (s, 1 H), 5.68 (d, 1 H, J=15 Hz), 5.40 (d, 1 H, J=15 Hz), 5.29 (s, 2 H), 4.95 (br s, 1 H), 4.27–4.00 (m, 2 H), 2.40 (s, 3 H), 2.36–2.13 (m, 2 H), 1.43 (s, 9 H), 1.0.1–0.95 (m, 12 H), 0.70 (s, 6 H).

To a solution of 10-acetoxy-20-O-(N-(tert-butoxycarbonyl)glycyl)-7-(tert-butyldimethylsilyl)camptothecin (21 mg, 0.031 mmol) in dichloromethane (5 ml) was added trifluoroacetic acid (2.5 ml). After stirring for 90 minutes, the mixture was concentrated under vacuum. The residue was dissolved in methanol-toluene (1:1, 4 ml). The solution was concentrated under vacuum. This procedure was repeated two more times to provide 10-acetoxy-7-(tert-butyldimethylsilyl)-20-O-(glycyl)camptothecin trifluoroacetic acid salt which was used in the next step without addition purification. $^1$H NMR (300 MHz, CD$_3$OD) δ 8.21–8.11 (m, 2 H), 7.68–7.63 (m, 1 H), 7.42 (s, 1 H), 5.69–5.38 (m, 4 H), 4.22 (q, 2 H, J=18 Hz), 2.39 (s, 3 H), 2.33–2.20 (m, 2 H), 1.07 (t, 3 H, J=8 Hz), 1.00 (s, 9 H), 0.75 (s, 6 H).

4-Dimethylaminopyridine (12 mg, 0.098 mmol) and diisopropylcarbodiimide (0.37 ml of a 0.1 M solution in dimethylformamide) were added sequentially to a solution of 10-acetoxy-7-(tert-butyldimethylsilyl)-20-O-(glycyl) camptothecin trifluoroacetic acid salt (0.03 mmol) and poly-(L-glutamic acid) (64 mg) in dimethylformamide (5 ml). After stirring for 20 hours, the mixture was cooled in an ice bath and 10% aqueous sodium chloride solution (20 ml) was added over a period of 30 minutes. The pH of the mixture was lowered to 2 by the slow addition of 0.1 M hydrochloric acid. The precipitate was collected by centrifugation. The solid was suspended in water (10 ml) and again isolated after centrifugation. This sequence was repeated two more times and the solid was dried under vacuum. The solid was then suspended in 5% methanol-chloroform (10 ml) and treated with ultrasound for 90 minutes. The mixture was filtered and the collected solid was dried under vacuum to provide PG-gly-(7-t-BuMe$_2$Si-10-OAc-CPT) (69 mg, 84% mass balance) as a pale yellow solid. Integration of the $^1$H indicated a loading by weight of 15%. $^1$H NMR (300 MHz, CF$_3$CO$_2$D) δ 8.71 (br s CPT Ar—H), 8.17 (s, CPT Ar—H), 7.99–7.91 (m, CPT Ar—H), 6.00–5.58 (m, CPT lactone, C5 —CH$_2$—), 5.00–4.77 (m, PG α-CH), 3.84 (s, Gly CH$_2$), 2.78–2.59 (m, PG -CH$_2$—), 2.38–2.05 (m, PG -CH$_2$—), 1.30 (br s, CPT —CH$_2$CH$_3$), 1.12 (br s, CPT (CH$_3$)$_3$CSi (CH$_3$)$_2$), 0.88 (br s, CPT (CH$_3$)$_3$CSi(CH$_3$)$_2$).

Example 20

In vivo Biological Activities

A. Camptothecin Conjugates

The maximum tolerated dose (MTD) and relative efficacy of PG-CPT conjugates was initially tested using single IP injections in C57BL/6 mice carrying subcutaneous B16 melanomas. Although B16 melanoma is only weakly responsive to 20(S)-camptothecin, this model is used to screen various compounds for preliminary efficacy assessment due to its reproducibility and the ability to evaluate a compound in a short time period. Tumors were produced in the muscle of the right interscapular region by subcutaneously injecting 1.0×10$^5$ murine melanoma cells (B-16-F0; ATTC CRL-6322) in a volume of 0.2 ml PBS supplemented with 2% FBS. Test compounds and vehicle control were administered (0.5 ml per 20 g body weight) 7 or 8 days after tumor cell implantation when the tumors had grown to 5±1 mm³. Camptothecin conjugates were dissolved in a 0.1 M Na₂HPO₄ solution by sonication at 45° C. for 45–60 minutes. Native camptothecins were dissolved in a mixture of 8.3% Cremophor EL/8.3% ethanol in 0.75% saline. All injections were given intraperitoneally (IP). Each treatment group consisted of 10 mice randomly allocated to each group. Tumor volume was calculated according to the formula (length×width×height)/2. Mice with tumors equal to or greater than 2000 mm³ were euthenized by cervical dislocation. Tumor efficacy of test compounds was determined by calculating the tumor growth delay (TGD): the average time in days for the tumors in the treatment group to reach a fixed volume minus the average time for the tumors in the control group to reach the same volume. An unpaired Student's t-test was done to determine statistical differences. The compounds were tested at different concentrations to determine their MTD. The MTD is the maximum tolerated equivalent camptothecin dose. The MTD for PG-20(S)-camptothecin conjugates was found to be approximately 2-fold higher than that for free 20(S)-camptothecin, thus allowing administration of higher doses of camptothecin resulting in enhanced anti-tumor efficacy.

For directly coupled 20(S)-camptothecin, PG-CPT, the maximum loading was approximately 14% (weight of 20(S)-camptothecin/total weight of conjugate). A glycine linker (PG-gly-CPT) allowed loading of up to 39% and enhanced aqueous solubility.

B. Effect of Various PG-camptothecin Conjugates on Tumor Growth Using Animal Models In general, it was found that PG-glycine conjugates of 20(S)-camptothecin were superior to PG-CPT conjugates made with other linkers (biologically i.e. efficacy and toxicity and/or with respect to solubility in aqueous media, and ease of synthesis and amount of camptothecin that could be loaded on the PG backbone) and to comparable PG-gly-conjugates consisting of 20(S)-9-aminocamptothecin, 20(S)-10-hydroxycamptothecin, 20(S)-7-ethyl-10-hydroxycamptothecin (SN 38) and 20(S)-10-acetoxy-7-(tert-butyldimethylsilyl) camptothothecin (10-Oacetyl DB 67). The data to support this claim are summarized below.

In some of the experiments PG conjugates were compared to unconjugated 20(S)-camptothecin or commercially and clinically available topotecan. In all cases PG-conjugates showed better anti-tumor efficacy than the free drugs.

In addition, single dose efficacy studies in two other tumor models (MCA-4 breast cancer and OCA-1 ovarian cancer) demonstrated that PG-CPT, either directly coupled or using a glycine linker also had enhanced efficacy compared with native 20(S)-camptothecin at its MTD and that the MTD of PG conjugates was approximately 2-fold higher than the MTD for naïve CPT. In addition to the above-mentioned models, one other syngeneic model was used viz. LL/2 Lewis lung (ATTC CRL-1642) and 2 xenogeneic models were used viz. human NCI-H460 lung carcinomas (ATTC HTB-177) and HT-29 human colon carcinomas (ATTC HTB-38). In these xenogeneic models instead of immunocompetent C57BL/6 mice, immunocompromised athymic ncr nu/nu mice were used. Except for the number of tumor cells implanted to generate tumors the experimental protocol and procedures were identical to that for the B-16/F0 model.

A total of 6 linkers other than glycine were used to make PG conjugates of 20(S)-camptothecin. In all conjugates, the PG was from the same lot and had an average MW of 50 kD. The different conjugates were tested and compared to PG-gly-CPT in a number of experiments using the B-16 model. First it was demonstrated that glycine conjugates are more efficacious than 2-hydroxyacetic acid (glycolic acid) conjugates at all three 20(S)-camptothecin concentrations tested. Secondly, it was demonstrated that glycine conjugates were significantly more efficacious in the B-16 model than conjugates made with: glutamic acid (glu), alanine (ala), β-alanine (β-ala) and 4-aminobutyric acid.

The loading of these conjugates varied from 22% for β-ala linked 20(S)-camptothecin to 37% for gly-linked 20(S)-camptothecin. Another linker evaluated and compared with gly was 4-hydroxybutyric acid. The two conjugates had the same amount of 20(S)-camptothecin loading (35%) and were compared in a number of assays using the B-16/F0, LL/2 and HT-29 models. It was demonstrated that glycine conjugates were equally or more efficacious than the 4-hydroxybutyric acid conjugates. In addition, 4-hydroxybutyric acid conjugates are more difficult to synthesize, are less soluble in aqueous solutions than glycine conjugates and may have undesired effects.

The effect of the length of the linker in a number of experiments was studied using the HT-29 and NCI-H460 models. The efficacy of conjugates consisting of gly (e.g., PG-gly-CPT), gly-gly (dimer) (e.g., PG-gly-gly-CPT), or gly-gly-gly (trimer) (e.g., PG-gly-gly-gly-CPT) as linker with equal 20(S)-camptothecin loading was compared. The rationale for this was that (theoretically) a longer linker might lead to a more stable form of the PG-CPT conjugate. It appeared that the trimer-containing conjugates were more efficacious than the monomer- and dimer-containing conjugates (which show identical efficacy) at the same % 20(S)-camptothecin loading and equivalent 20(S)-camptothecin concentrations. However, the trimer-containing conjugates are more toxic than mono-gly conjugates at the same 20(S)-camptothecin equivalent concentrations. In addition, the synthesis of dimer- and trimer-containing conjugates is more time consuming than glycine conjugates and the water solubility of trimer-containing conjugates is significantly lower than that of mono-gly conjugates.

Important parameters that could determine the efficacy and toxicity of the conjugates are among others, the average molecular weight of the PG and the % 20(S)-camptothecin loading. It was demonstrated using the B-16 and HT-29 models that PG-gly-CPT conjugates made with PG of 50 kD were more efficacious than those made with PG of either 74 kD or 33 kD. Thus it was decided to focus on 50 kD PG-gly-conjugates only and to examine the effect of varying 20(S)-camptothecin loading on the anti-tumor efficacy. It was found in an initial experiment using HT-29 colon carcinomas that 35% loading was clearly more efficacious than 25%, 20% or 15% loaded conjugates, while mice received the same amount of 20(S)-camptothecin equivalents. Increasing the loading from 35% to 37% and 39% further increased the efficacy in the HT-29 and also the NCI-H460 model. Increasing loading to 47% did not result in better efficacy; in fact the efficacy was less than the 35% loaded material. The water solubility of the conjugates decreases somewhat between 35% and 39%, with the higher loaded material being the most difficult to dissolve.

In one experiment using the HT-29 model it was demonstrated that the efficacy of a single intraperitoneal (ip) dose of 50 kD PG-gly-CPT could be further enhanced by dosing the mice 4 times with a weekly interval for a total accumulative camptothecin dose 3 times that of given in the single dose. This dosing regimen was very well tolerated by the mice.

The ideal PG-gly-CPT conjugate consists of PG with average MW of 50 kD (measured by viscosity), (mono)

glycine as a linker and 35–37% 20(S)-camptothecin. The MTD in male ncr nu/nu mice is 40 mg/kg 20(S)-camptothecin equivalents and is approximately 2-fold higher than the MTD for free 20(S)-camptothecin.

C. Other Human Tumor Models

The antitumor activity of PG-gly-CPT (33 kD, 37% loaded) on NCI-H322 (ATTC CRL-5806) human lung cancer inoculated s.c. in female nude mice was studied. The drug was injected i.v. on days 9, 13, 17 and 21 at a 20(S)-camptothecin equivalent dose of 40 mg/kg when tumors measured 7–8 mm in diameter. The TGD was 40 days.

Female nude mice with 7–8 mm subcutaneous NCI-H460 human non-small cell lung cancer xenografts were treated with PG-gly-CPT on days 1, 5, 9, and 13 at a dose of 40 mg/kg 20(S)-camptothecin per injection. The tested dose of 40 mg eq. 20(S)-camptothecin/kg every 4th day ×4 modestly exceeded the MTD. Although there were no deaths, weight loss was approximately 20% of the starting weight. The absolute tumor growth delay (defined as difference in days for tumors to grow from 8 mm to 12 mm between the treated and the control groups) was 43 days for the PG-gly-CPT treated mice. In a second experiment, directly conjugated PG-CPT was tested i.p. on the same schedule and also produced substantial growth delay without observable toxicity.

PG-gly-CPT was also tested in female nude mice inoculated s.c. with 1.5×10⁶ cells/mouse of NCI-H1299 (ATTC CRL-5803) human lung cancer cells. Due to excessive weight loss at 40 mg eq. 20(S)-camptothecin/kg in the prior experiment in nude mice, the dose was lowered to 30 mg eq. 20(S)-camptothecin/kg every 4th day×4. This dose was well-tolerated and a TGD of 32 days was observed.

D. 10-Hydroxycamptothecin Conjugates

PG-conjugates of 20(S)-10-hydroxycamptothecin have undergone preliminary studies in the B16 model. The most active-conjugate in these studies is the material directly conjugated or glycine linked through the 20-hydroxyl group. In initial experiments, the directly coupled material PG-(10-OAc-CPT) appeared more active at 50 mg eq. 20(S)-10-hydroxycamptothecin/kg than PG-gly-(10-O-CPT). However, this dose was below the MTD for both compounds and the PG-(10-OAc-CPT) solution was very viscous and the compound precipitated out of solution after approx. 30 min, thus making it impractical to work with.

At 50 mg eq. 20(S)10-hydroxycamptothecin/kg, PG-(10-OAc-CPT) produced a TGD of 5.3 days (p<0.01 compared to control). It is of interest that the MTD for PG-(10-OH-CPT) is between 10 and 50 mg eq 20(S)-10-hydroxycamptothecin/kg. However, even at the toxic dose of 50 mg/kg, it was not as effective as the PG-(10-OAc-CPT) or the PG-gly-(10-OH-CPT).

It is of interest to note that in a direct comparison using the B-16/F0 model, the 50 kD PG-gly-(10-OH-CPT) conjugate was approximately twice as efficacious as PG-gly-(7-Et-10-OH-CPT); at the same percentage loading and SN 38 concentration. The same observation was made when we compared PG-gly-CPT with PG-gly-(7-t-BuMe₂Si-10-OAc-CPT) using the HT-29 model. In general it was found that PG-20(S)-10-hydroxycamptothecan conjugates and PG conjugates of 10-hydroxycamptothecin derivatives or (7-t-BuMe₂Si-10-OAc-CPT) were not as efficacious, well tolerated or easy to dissolve in aqueous solutions as the PG-gly-20(S) camptothecin conjugates; regardless if they were directly linked or glycine linked, or linked at different positions.

E. 9-amino Camptothecin Conjugates

Studies indicate that PG-9-NH-CPT is active and has a MTD in excess of 25 mg eq. 20(S)-9-aminocamptothecin/kg. It has been found, however that 20(S)-9-aminocamptothecin conjugates, were not as efficacious, well tolerated or easy to dissolve in aqueous solutions as the PG-gly-20(S) camptothecin conjugates; regardless if they were directly linked or glycine linked, or linked through an ester bond or amide bond, or linked at different positions.

F. Summary and Comparative Data

In direct comparisons with PG-gly-20(S)-CPT conjugates neither the PG conjugates made with 20(S)-9-aminocamptothecin, nor those made with 20(S)-10-hydroxycamptothecin were as efficacious, well tolerated and easy to dissolve in aqueous solutions as the PG-gly-CPT conjugates, regardless if they were directly linked or glycine linked, or linked through an ester bond or amide bond (in case of 20(S)-9-aminocamptothecin), or linked at different positions.

TABLE 2

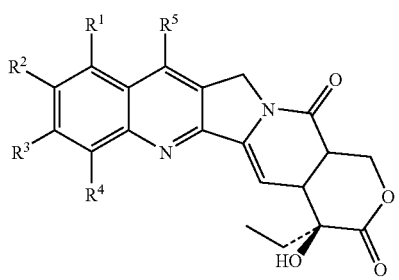

where R⁴ = H

| Compound | R⁵ | R¹ | R² | R³ |
|---|---|---|---|---|
| 20(S)-camptothecin | H | H | H | H |
| topotecan | H | CH₂N(CH₃)₂ | OH | H |
| 20(S)-9-amino camptothecin | H | NH₂ | H | H |
| 20(S)-9-nitro camptothecin | H | NO₂ | H | H |

TABLE 2-continued where R⁴ = H

| Compound | $R^5$ | $R^1$ | $R^2$ | $R^3$ |
|---|---|---|---|---|
| 10-hydroxy-camptothecin | H | H | OH | H |
| SN-38 | $CH_2CH_3$ | H | OH | H |
| 20(S)-10,11-methylenedioxy-camptothecin | H | H | —$CH_2$—O—$CH_2$— | |
| Lurtotecan (GI 147211) | —$CH_2$-(N-methyl piperazine) | H | —O—$CH_2$—$CH_2$—O— | |
| Irinotecan (CPT-11) | $CH_2CH_3$ | H | OCO-[1,4'-bipiperidinyl] | H |
| DX-8951F | —$CH_2$—$CH_2$—$CH(NH_2)$— | | $CH_3$ | F |
| DB 67 | —$SiMe_2$t-Bu | H | —OH | H |

TABLE 3

| PG Conugate | % CPT in conjuqate (w/w) | Aqueous solubility | Diagnostic signals in 300 MHz $^1$H NMR Spectra (DMSO-d6) | Murine single dose MTD (IP) (mg eq. CPT/kg) |
|---|---|---|---|---|
| PG-CPT (20-conjugated) | 14 | 11 mg/ml | δ 12.1 (broad singlet, PG γ-COO$\underline{H}$), 7.4–8.5 (multiple broad signals, Ar—$\underline{H}$), 5.6 (broad singlet, lactone —C$\underline{H}_2$—), 0.9 (broad signal, CPT $CH_2C\underline{H}_3$) | 60–80 mg eq. CPT/kg |
| PG-gly-CPT (20-conjugated) | 37 | 25 mg/ml | δ 12.1 (broad singlet, PG γ-COO$\underline{H}$), 7.4–8.5 (multiple broad signals, Ar—$\underline{H}$), 5.6 (broad singlet, lactone —C$\underline{H}_2$—), 0.9 (broad signal, CPT $CH_2C\underline{H}_3$) | 60–80 mg eq. CPT/kg |
| PG-(10-OAc-CPT) (20-conjugated) | 13 | 10 mg/ml | δ 12.1 (broad singlet, PG γ-COOH), 7.2–8.6 (multiple broad signals, Ar—$\underline{H}$); 5.4 (singlet, lactone —C$\underline{H}_2$—); 5.2 (singlet, C5-$\underline{H}_2$); 0.9 (broad tripiet, CPT $CH_2C\underline{H}_3$) | 10–20 mg eq. CPT/kg |
| PG-(10-O-CPT) (10-conjugated) | 13 | 10 mg/ml | δ 12.1 (broad singlet, PG γ-COOH), 7.2–8.6 (multiple broad signals, Ar—$\underline{H}$); 5.4 (singlet, lactone —C$\underline{H}_2$—); 5.2 (singlet, C5-$\underline{H}_2$); 0.9 (broad triplet, CPT $CH_2C\underline{H}_3$) | 50 mg eq. CPT/kg |
| PG-gly-(10-O-CPT) (10-linked) | 20 | >10 mg/ml | δ 12.1 (broad singlet, PG γ-COOH), 7.2–8.8 (multiple broad signals, Ar—$\underline{H}$); 5.4 (singlet, lactone —C$\underline{H}_2$—); 5.2 (singlet, C5-$\underline{H}_2$); 0.9 (broad signal, CPT $CH_2C\underline{H}_3$) | >10<50 mg eq. CPT/kg |
| PG-(10-OH-CPT) (20-linked) | 19 | >10 mg/ml | δ 12.1 (broad singlet, PG γ-COOH), 7.0–8.5 (multiple broad signals, Ar—$\underline{H}$); 5.4 (singlet, lactone —C$\underline{H}_2$—); 5.2 (singlet, C5-$\underline{H}_2$); 0.9 (broad signal, CPT $CH_2C\underline{H}_3$) | >50 mg eq. CPT/kg |
| PG-(9-NH-CPT) (9-conjugated) | 14 | 7 mg/ml | δ 12.1 (broad singlet, PG γ-COOH), 8.8 (broad singlet, C7-$\underline{H}$), 7.2–8.0 (multiple broad signals, Ar—$\underline{H}$), 5.4 (broad singlet, lactone —C$\underline{H}_2$—), 0.9 (broad signal, CPT $CH_2C\underline{H}_3$). | >25 mg eq. CPT/kg |

TABLE 4

| PG Conjugate[a] | CPT Loading[b] | Dose (mg CPT/kg) | TGD (days to 500 mm³) | | | MTD (mg CPT/kg) |
| | | | B16 | HT-29 | NCI-H460 | |
|---|---|---|---|---|---|---|
| PG-CPT[c] | 20 | 80? | 4.0 | — | — | >80 |
| | 32 | 35 | 3.3 | — | — | |
| | 19 | 33 | — | 4.1 | — | |

TABLE 4-continued

| PG Conjugate[a] | CPT Loading[b] | Dose (mg CPT/kg) | TGD (days to 500 mm³) B16 | HT-29 | NCI-H460 | MTD (mg CPT/kg) |
|---|---|---|---|---|---|---|
| PG-gly-CPT | 33 | 33 | — | 11.9 | — | ~40 |
|  | 33 | 38 | — | 20.3 | 15.8 |  |
|  | 39 | 40 | — | 25.8 | 38.5 |  |
|  | 47 | 40 | — | 5.8 | 6.5 |  |
| PG-gly-gly-CPT | 19 | 33 | — | 4.5 | — | ≧33 |
| PG-gly-gly-gly-CPT | 19 | 33 | — | 6.9 | — | ≦34 |
|  | 30 | 34 | — | 28.4 | 38.5 |  |
| PG-ala-CPT | 20 | 73 | 2.2 | — | — | ≧73 |
| PG-(β-ala)-CPT | 31 | 67 | 1.1 | — | — | ≧67 |
| PG-(4-NH-butyryl)-CPT | 32 | 80 | 0.9 | — | — | ≧80 |
| PG-(2-O-acetyl)-CPT | 15 | 80 | 3.8 | — | — | ≧80 |
| PG-(4-O-butyryl)-CPT | 32 | 37 | 2.8 | — | — | ~36 |
|  | 24 | 36 | — | 13.1 | — |  |
| PG-(γ-glu)-CPT | 21 | 54 | 0.8 | — | — | ≧54 |

[a]Molecular weight of PG used in the preparation of these PG-camptothecin conjugates was 50 kD (viscosity) unless specified otherwise.
[b]% Loading = [(weight of CPT in PG-CPT sample) ÷ (weight of PG-CPT sample)] × 100.
[c]Molecular weight of PG used in the preparation of PG-CPT was 33 kD (viscosity).
[d]Solution was turbid.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto. All patents, patent applications and publications cited herein are incorporated by reference in their entirety.

What is claimed is:

1. A composition comprising a polyglutamic acid-camptothecin conjugate having the formula:

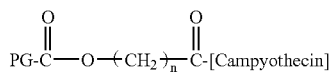

wherein:
PG is polyglutamic acid polymer;
Camptothecin is 20(S)-camptothecin or a biologically active 20(S)-camptothecin analog linked via the oxygen at position 20 of Camptothecin;
wherein the 20(S)-camptothecin analog is of the formula

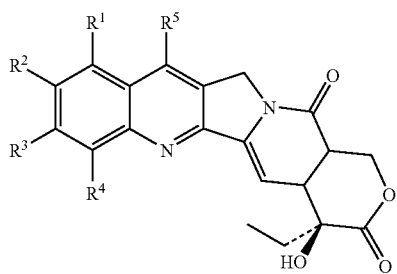

wherein one or more of $R_1$–$R_5$ is other than H and n is an integer between 1 and 10;
PG is attached to the moiety —O—$(CH_2)_n$—C(O)-[Camptothecin] through the γ-carbonyl group of a monomeric unit of said polyglutamic acid polymer.

2. The composition of claim 1, wherein the weight % ratio of said camptothecin to said PG is about 1–60%.

3. The composition of claim 1, wherein the weight % ratio of said camptothecin to said PG is 1–45%.

4. The composition of claim 1, wherein the weight % ratio of said camptothecin to said PG is 25–50%.

5. The composition of claim 1, wherein the weight % ratio of said camptothecin to said PG is 27–40%.

6. The composition of claim 1, wherein the weight % ratio of said camptothecin to said PG is 30–50%.

7. The composition of claim 1, wherein the weight % ratio of said camptothecin to said PG is 30–47%.

8. The composition of claim 1, wherein the weight % ratio of said camptothecin to said PG is 30–45%.

9. The composition of claim 1, wherein the weight % ratio of said camptothecin to said PG is 30–40%.

10. The composition of claim 1, wherein the weight % ratio of said camptothecin to said PG is 30–37%.

11. The composition of claim 1, wherein the weight % ratio of said camptothecin to said PG is 30–35%.

12. The composition of claim 1, wherein the weight % ratio of said camptothecin to said PG is 35–47%.

13. The composition of claim 1, wherein the weight % ratio of said camptothecin to said PG is 35–45%.

14. The composition of claim 1, wherein the weight % ratio of said camptothecin to said PG is 35–40%.

15. The composition of claim 1, wherein the weight % ratio of said camptothecin to said PG is 35–39%.

16. The composition of claim 1, wherein said camptothecin analog is selected from the group consisting of 20(S)-camptothecin, 20(S)-topotecan; 20(S)-9-aminocamptothecin; 20(S)-9-nitrocamptothecin; 20(S)-i 10-hydroxycamptothecin; SN-38; 20(S) -10,11 -methylenedioxycamptothecin; lurtotecan; irinotecan; DX-8951 F or DB 67.

17. The composition of claim 1, wherein said camptothecin analog is selected from 20(S)-camptothecin, 20(S)-9-aminocamptothecin, 20(S)-9-nitrocamptothecin, 20(S)-7-ethyl-10-hydroxycamptothecin, 20(S)-i 10-hydroxycamptothecin and 20(S)-10-acetoxycamptothecin.

18. The composition of claim 17, wherein said camptothecin analog is 20(S)-camptothecin.

19. A method of preparing a composition comprising a polyglutamic acid-camptothecin conjugate of claim 1 wherein said method comprises:
  (a) providing a polyglutamic acid polymer having a MW of about 25,000 to about 60,000 daltons, as determined by viscosity, and HO—$(CH_2)_n$—C(O)-[Camptothecin], or a protected form thereof, for conjugation thereto; and
  (b) covalently linking said HO—$(CH_2)_n$—C(O)[Camptothecin] to said polyglutamic acid polymer under conditions sufficient to attach at least 5 moles of 20(S)-camptothecin per mole of polymer, thereby forming said polyglutamic acid-camptothecin conjugate.

20. The composition of claim 19, wherein the weight % ratio of said camptothecin to said PG is 15–50%.

21. The composition of claim 19, wherein the weight % ratio of said camptothecin to said PG is 1–45%.

22. The composition of claim 19, wherein the weight % ratio of said camptothecin to said PG is 25–50%.

23. The composition of claim 19, wherein the weight % ratio of said camptothecin to said PG is 27–40%.

24. The composition of claim 19, wherein the weight % ratio of said camptothecin to said PG is 30–50%.

25. The composition of claim 19, wherein the weight % ratio of said camptothecin to said PG is 30–47%.

26. The composition of claim 19, wherein the weight % ratio of said camptothecin to said PG is 30–45%.

27. The composition of claim 19, wherein the weight % ratio of said camptothecin to said PG is 30–40%.

28. The composition of claim 19, wherein the weight % ratio of said camptothecin to said PG is 30–37%.

29. The composition of claim 19, wherein the weight % ratio of said camptothecin to said PG is 30–35%.

30. The composition of claim 19, wherein the weight % ratio of said camptothecin to said PG is 35–47%.

31. The composition of claim 19, wherein the weight % ratio of said camptothecin to said PG is 35–45%.

32. The composition of claim 19, wherein the weight % ratio of said camptothecin to said PG is 35–40%.

33. The composition of claim 19, wherein the weight % ratio of said camptothecin to said PG is 35–39%.

34. A pharmaceutical composition for the treatment of cancer, comprising an effective amount of the polyglutamic acid-camptothecin conjugate of claim 1 or a pharmaceutically acceptable salt thereof and a pharmaceutically acceptable carrier and/or diluent.

35. The pharmaceutical composition of claim 34, wherein said camptothecin is 20(S)-camptothecin.

36. The composition of claim 34, wherein the weight % ratio of said camptothecin to said PG is 15–50%.

37. The composition of claim 34, wherein the weight % ratio of said camptothecin to said PG is 1–45%.

38. The composition of claim 34, wherein the weight % ratio of said camptothecin to said PG is 25–50%.

39. The composition of claim 34, wherein the weight % ratio of said camptothecin to said PG is 27–40%.

40. The composition of claim 34, wherein the weight % ratio of said camptothecin to said PG is 30–50%.

41. The composition of claim 34, wherein the weight % ratio of said camptothecin to said PG is 30–47%.

42. The composition of claim 34, wherein the weight % ratio of said camptothecin to said PG is 30–45%.

43. The composition of claim 34, wherein the weight % ratio of said camptothecin to said PG is 30–40%.

44. The composition of claim 34, wherein the weight % ratio of said camptothecin to said PG is 30–37%.

45. The composition of claim 34, wherein the weight % ratio of said camptothecin to said PG is 30–35%.

46. The composition of claim 34, wherein the weight % ratio of said camptothecin to said PG is 35–47%.

47. The composition of claim 34, wherein the weight % ratio of said camptothecin to said PG is 35–45%.

48. The composition of claim 34, wherein the weight % ratio of said camptothecin to said PG is 35–40%.

49. The composition of claim 34, wherein the weight % ratio of said camptothecin to said PG is 35–39%.

50. A method of treating cancer, comprising administering to a patient in need of such treatment a pharmaceutical composition according to claim 34, thereby effecting treatment of said cancer.

51. The pharmaceutical composition of claim 50, wherein said camptothecin is 20(S)-camptothecin.

52. The composition of claim 50, wherein the weight % ratio of said camptothecin to said PG is 15–50%.

53. The composition of claim 50, wherein the weight % ratio of said camptothecin to said PG is 20–45%.

54. The composition of claim 50, wherein the weight % ratio of said camptothecin to said PG is 25–50%.

55. The composition of claim 50, wherein the weight % ratio of said camptothecin to said PG is 27–40%.

56. The composition of claim 50, wherein the weight % ratio of said camptothecin to said PG is 30–50%.

57. The composition of claim 50, wherein the weight % ratio of said camptothecin to said PG is 30–47%.

58. The composition of claim 50, wherein the weight % ratio of said camptothecin to said PG is 30–45%.

59. The composition of claim 50, wherein the weight % ratio of said camptothecin to said PG is 30–40%.

60. The composition of claim 50, wherein the weight% ratio of said camptothecin to said PG is 30–37%.

61. The composition of claim 50, wherein the weight % ratio of said camptothecin to said PG is 30–35%.

62. The composition of claim 50, wherein the weight % ratio of said camptothecin to said PG is 35–47%.

63. The composition of claim 50, wherein the weight % ratio of said camptothecin to said PG is 35–45%.

64. The composition of claim 50, wherein the weight % ratio of said camptothecin to said PG is 35–40%.

65. The composition of claim 50, wherein the weight % ratio of said camptothecin to said PG is 35–39%.

66. The composition of claim 1, wherein the 20(S)-camptothecin analog is selected from the group consisting of topotecan, 20(S)-9-amino camptothecin, 20(S)-9-nitro camptothecin, 10-hydroxy-camptothecin, SN-38, 20(S)-10, 11-methylenedioxycampto-thecin, Lurtotecan, Irinotecan, DX-8951F, DB 67.

67. The composition of claim 1, wherein $R_4$ is H and
  (a) $R^1$ is $CH_2N(CH_3)_2$, $R^2$ is OH, $R^3$ is H, and $R^5$ is H; or
  (b) $R^1$ is $NH_2$ and $R^2$, $R^3$, and $R^5$ are H; or
  (c) $R^1$ is $NO_2$ and $R^2$, $R^3$, and $R^5$ are each H; or
  (d) $R^2$ is OH and $R^1$, $R^3$, and $R^5$ are each H; or
  (e) $R^1$ is H, $R^2$ is OH, $R^3$ is H, and $R^5$ is $CH_2CH_3$; or
  (f) $R^1$ and $R^5$ are each H and $R^2$ and $R^3$ are each —$CH_2$—O—$CH_2$-; or
  (g) $R^1$ is H, $R^2$ and $R^3$ are each —O—$CH_2$—$CH_2$—O—, and $R^5$ is —$CH_2$—(N-methyl piperazine); or
  (h) $R^1$ and $R^3$ are each H, $R^2$ is OCO-[1,4'-bipiperidinyl], and $R^5$ is $CH_2CH_3$; or
  (i) $R^1$ and $R^5$ are each —$CH_2$—$CH_2$—$CH(NH_2)$—, $R^2$ is $CH_3$, and $R^3$ is F; or
  (j) $R^1$ and $R^3$ are each H, $R^2$ is —OH, and $R^5$ is —$SiMe_2$t-Bu.

* * * * *